(12) United States Patent
Siu

(10) Patent No.: US 6,490,047 B2
(45) Date of Patent: Dec. 3, 2002

(54) SYSTEM AND METHOD FOR LASER ULTRASONIC BOND INTEGRITY EVALUATION

(76) Inventor: Bernard K. Siu, 451 W. Lambert Rd. Suite 11, Brea, CA (US) 92821

( * ) Notice: Subject to any disclaimer, the term of this patent is extended or adjusted under 35 U.S.C. 154(b) by 0 days.

(21) Appl. No.: 09/771,349

(22) Filed: Jan. 26, 2001

(65) Prior Publication Data

US 2002/0043109 A1 Apr. 18, 2002

Related U.S. Application Data

(63) Continuation of application No. 09/215,374, filed on Dec. 18, 1998, now Pat. No. 6,181,431.
(60) Provisional application No. 60/068,362, filed on Dec. 19, 1997.

(51) Int. Cl.[7] .................................................. G01B 9/02
(52) U.S. Cl. ....................................... 356/502; 356/432
(58) Field of Search ................................ 356/432, 502; 73/655, 657

(56) References Cited

U.S. PATENT DOCUMENTS

| | | |
|---|---|---|
| 3,982,811 A | 9/1976 | Siu et al. |
| 4,659,224 A | 4/1987 | Monchalin |
| 4,966,459 A | 10/1990 | Monchalin |
| 5,080,491 A | 1/1992 | Monchalin et al. |
| 5,103,676 A | 4/1992 | Garcia et al. |
| 5,137,361 A | 8/1992 | Heon et al. |
| 5,201,841 A | 4/1993 | Lebeau et al. |
| 5,260,772 A | 11/1993 | Pollak et al. |
| 5,270,797 A | 12/1993 | Pollak et al. |
| 5,302,836 A | 4/1994 | Siu |
| 5,420,689 A | 5/1995 | Siu |
| 5,424,838 A | 6/1995 | Siu |
| 5,535,006 A | 7/1996 | Telschow et al. |
| 5,633,711 A | 5/1997 | Nelson et al. |
| 6,181,431 B1 | 1/2001 | Siu |

FOREIGN PATENT DOCUMENTS

| | | |
|---|---|---|
| JP | 62-7198 | 10/1987 |
| WO | WO 99/00641 | 1/1997 |

OTHER PUBLICATIONS

Nelson et al, "Optical generation of tunable ultraonic waves", Journal of Applied Physics, Feb. 1992, pp. 1144–1149.

Primary Examiner—Samuel A. Turner
(74) Attorney, Agent, or Firm—David S. Alavi

(57) ABSTRACT

A nondestructive bond testing system is implemented using a pulse laser that sends a single or multiple pulse(s) of controlled magnitude and bombards an object of interest causing a thermoelastic excitation response. This excitation in turn induces an ultrasonic propagation along or through the surface material. By detecting, capturing and interpreting these thermoelastic propagation signatures, the attachment condition of the joining materials is determined. The technique is a significant improvement over traditional mechanical pull, shear or contact type techniques. The techniques are implemented in automated high speed inspection systems suitable for real time manufacturing application. Particular applications include evaluating material joining in microelectronics manufacture (such as ball bonds) and thin coating processes.

32 Claims, 17 Drawing Sheets

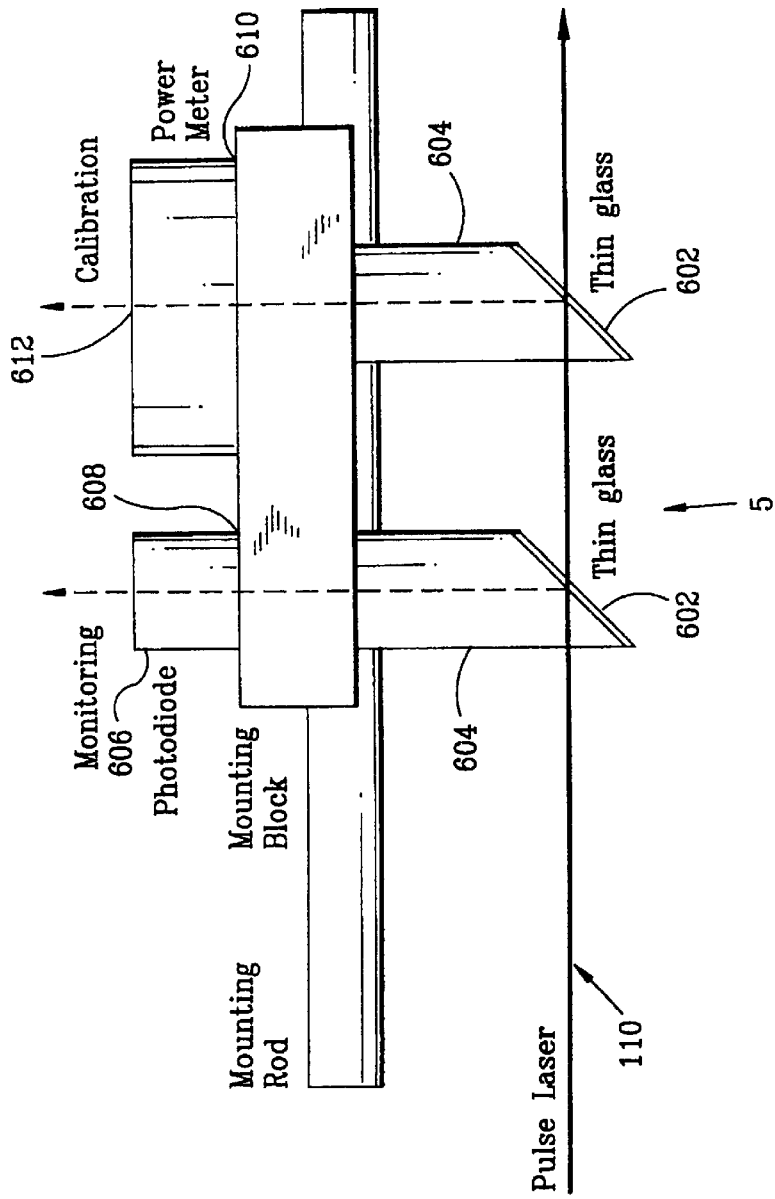

SYSTEM AND METHOD FOR LASER ULTRASONIC BOND INTEGRITY EVALUATION

RELATED APPLICATIONS

This application is a continuation of prior-filed non-provisional application Ser. No. 09/215,374 of the same title filed Dec. 18, 1998, now U.S. Pat. No. 6,181,431 said application being hereby incorporated by reference as if fully set forth herein. Said prior application in turn claims benefit of prior-filed provisional Application No. 60/068,362 filed Dec. 19, 1997, said provisional application being hereby incorporated by reference as if fully set forth herein.

GOVERNMENT RIGHTS

The U.S. Government has limited rights in this invention pursuant to contract No. N66001-95-C-7021 between the United States Navy and Simpex Technologies, Inc.

FIELD OF THE INVENTION

The present invention relates generally to an apparatus and method for determining bond integrity (adhesion status) of joined materials at a micro-level.

BACKGROUND OF THE INVENTION

There has been a long-felt need for non-destructive inspection methods that can be used to determine the integrity of a bond between two items. This need has been felt particularly in the case of bonds formed at the micro-level. The micro-level can be defined as involving at least one material with a dimension on the order of 0.005 inch or smaller. Such inspection methods might be applied to testing ball and wedge bonds, thin coatings, circuit traces, ribbon bonds, solder balls, surface mount components, PIN grid arrays, and MIMMs commonly used in microelectronics interconnects. The materials joined in these applications include, but are not limited to, silicon, silicon carbide, aluminum, gold, gallium arsenide and the like.

For example, ball bonds used in connecting silicon wafers to external circuits through very fine wires are typically tested, if at all, according to military specifications which require a pull test of each bond. This test is performed using a machine which sequentially hooks each wire and applies a predetermined pulling force to determine whether the associated bond will hold. This technique has significant limitations. In particular, the inventor has discovered that if this test is performed repeatedly on the wires of the same device, an increasing number of wires typically pull loose with each succeeding test. This result implies that the test does not truly qualify as non-destructive. That is, each application of a pulling force to a wire weakens its bond and repeated testing will actually break the bonds. It is possible that a bond might pass a single pull test of this type, but that the test would leave the bond precariously connected and destined for failure in the field when subjected to ambient vibration, shock, or temperature variations.

In the case of bonds having larger dimensions, such as pipe seams, welds used in automotive and marine manufacturing, etc. various x-ray and acoustic techniques have been applied to analyze the condition of an interface between two items. Laser ultrasound techniques have also been proposed. For example, U.S. Pat. No. 4,659,224 and U.S. Pat. No. 4,966,459 to Monchalin, U.S. Pat. No. 5,081,491, to Monchalin et al., and U.S. Pat. No. 5,137,361 to Heon et al. disclose the results of early research in this field. U.S. Pat. No. 5,103,676 to Garcia et al. shows a further method of laser ultrasonic process monitoring.

Laser techniques have also been considered for use with smaller bonds such as those found in semiconductor circuits. U.S. Pat. No. 5,201,841 to Lebeau et al. proposes a thermal gradient technique, and Japanese Patent Publication 62-7198 Jan. 14, 1987 by Hitachi Research Corp. appears to propose a laser technique.

The inventor's prior U.S. Pat. Nos. 5,420,689, 5,424,838, and 5,302,836 disclose lighting methods and apparatus useful in small-scale laser ultrasonic measurement. U.S. Pat. No. 5,535,006 to Siu et al. builds on the inventor's earlier work and discloses a method of evaluating integrity of adherence of a conductor bond to a substrate.

However, as far as the inventor is aware, none of these prior systems has provided an effective alternative to pull testing of wire bonds, or an effective method for analyzing thin film coating integrity at the micro-level. The results produced by the systems disclosed in the inventor's own prior patents, while encouraging, were not consistent enough for industrial application.

Thus, there is a need in industry for improved methods and systems of this type that will provide repeatable, accurate, and truly non-destructive testing capability.

SUMMARY

Therefore, it is a general object of the invention to provide an improved system and method for determining the bond integrity (adhesion) status of adjoining materials using laser ultrasonic techniques.

It is another general object of the invention to provide an improved system and method for determining the bond integrity (adhesion) status of adjoining materials using a pulse laser which applies heat onto the surface of interest, resulting in generation of a thermoelastic propagation (surface, bulk, air waves or combination thereof) in all directions from the pulse point, which can be detected using a stabilized continuous wave laser using interferometric techniques.

Another broad object of the invention is to provide an improved system and method that is particularly adapted to nondestructively test and evaluate the thickness and/or uniformity and adhesion characteristics of a thin coating of material applied to a substrate.

Another general object of the invention is to provide an improved system and method that is particularly adapted to nondestructively determine the bond integrity of joining materials at the micro-level, such as microelectronic interconnects, ball bonds, wedge bonds, circuit traces, surface mount components and MIMMs.

It is also an important object of the invention to provide an improved system and method for analyzing thermoelastic propagation signatures, single or in combination, to interpret bond integrity (adhesion) of adjoining materials, and determine whether they are fully bonded, partially bonded and touching yet non-bonded.

Another useful object of the invention is to provide a fully automated bond integrity determination system with particular applications in inspection and testing in microelectronics manufacturing processes.

An additional object of the invention is to provide improved operational timing and signature gathering methods and apparatus for use in a laser ultrasonic measuring system.

It is also an object of the invention to provide a laser ultrasonic measuring system with a vastly improved signal to noise ratio for detected wave propagation signatures.

A further object of the invention is to provide a method for correlating surface wave propagation to bond integrity in the context of a bond testing system.

These objects and others are achieved, in a preferred embodiment of the present invention, by providing a pulse laser and a continuous laser detector forming a cause and effect sensing device. The pulse laser sends a single or multiple pulse(s) of controlled magnitude and bombards the object of interest causing a thermoelastic excitation response. This excitation in turn induces an ultrasonic propagation along or through the surface material. By detecting, capturing and interpreting these thermoelastic propagation signatures, the attachment condition of the joining materials is determined. The technique is a significant improvement over traditional mechanical pull, shear or contact type techniques. The object need not be contacted by mechanical means, the excitation is much gentler than that required in a contact test, and the speed of the test is much faster than other automated manufacturing process, making it suitable for real-time process control purposes.

BRIEF DESCRIPTION OF THE DRAWINGS

FIG. 6 is a side view of a pulse laser calibration and synchronization apparatus according to the invention.

FIG. 7 is a timing chart showing the effect of a variable delay in component response to a command to activate the pulse laser and data capture on the identification and collection of data. The variation in response time is very large compared to the window during which useful data may be collected, making it difficult to select that window.

DETAILED DESCRIPTION OF THE PREFERRED EMBODIMENTS

The present invention will be described first in terms of an embodiment which is particularly useful in a variety of small scale bond testing applications. Such inspection methods may be applied to testing the bonding integrity of any materials at the micro level. The bonds tested may include, but are not limited to, ball and wedge bonds, thin coatings, circuit traces, ribbon bonds, welds, solder balls, surface mount components, PIN grid arrays, MIMMs, and various types of adhesion media and methods commonly used in microelectronics interconnects. The materials joined in these applications include, but are not limited to, silicon, silicon carbide, aluminum, gold, gallium arsenide and the like.

Figure 1:
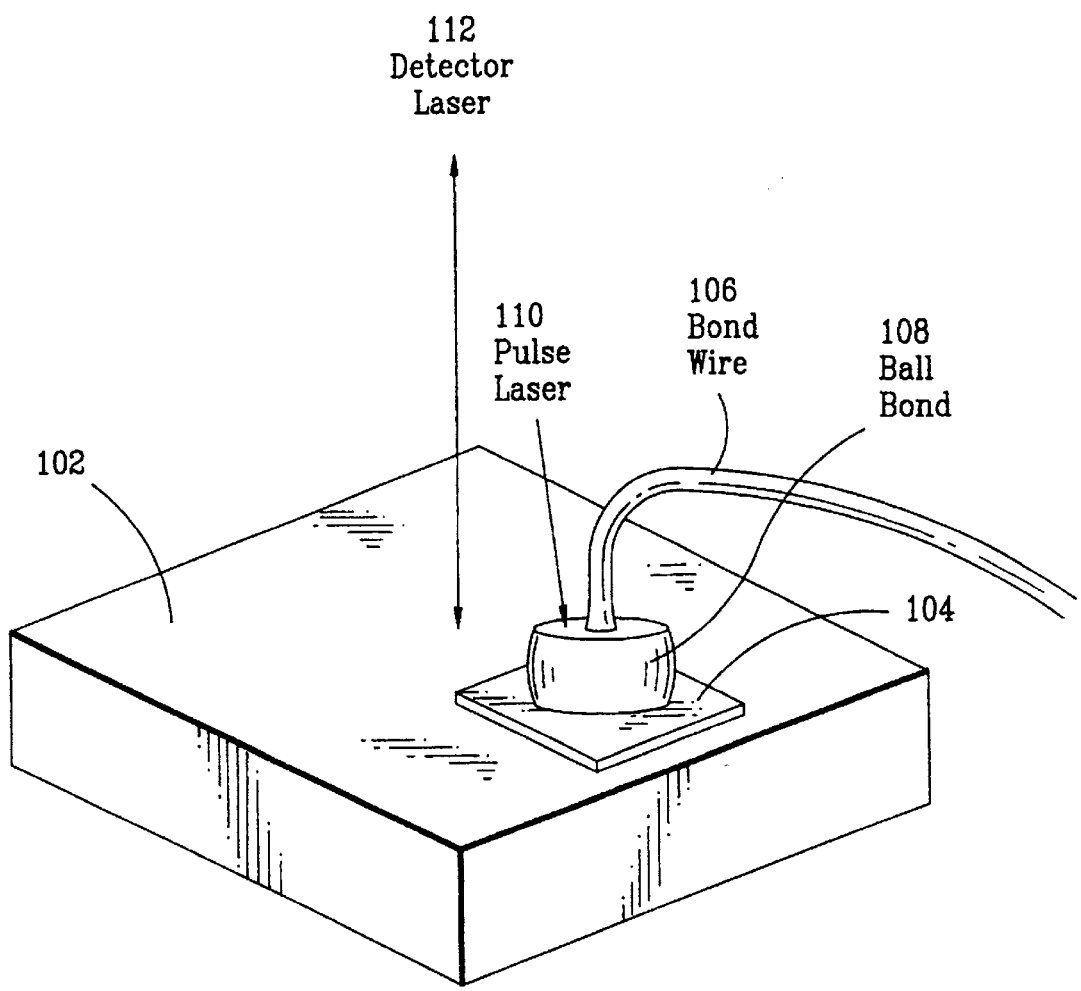
FIG. 1 is a view of a microelectronic ball bond showing the application of a pulse laser and detection laser for signature analysis.

One such application is the testing of the connection of a microelectronic ball bond or other small bond to its bonding pad, and the first embodiment of the invention will be described using this application as an example. FIG. 1 shows substrate 102, on which bond pad 104 is mounted. A bond wire 106 is connected via ball bond 108 to bond pad 104. A pulse laser beam 110 is applied to ball bond 108, while the reflection of detector laser beam 112 is used to detect vibrations propagating through substrate 102 as a result of the application of pulse laser beam 110.

Figure 2:
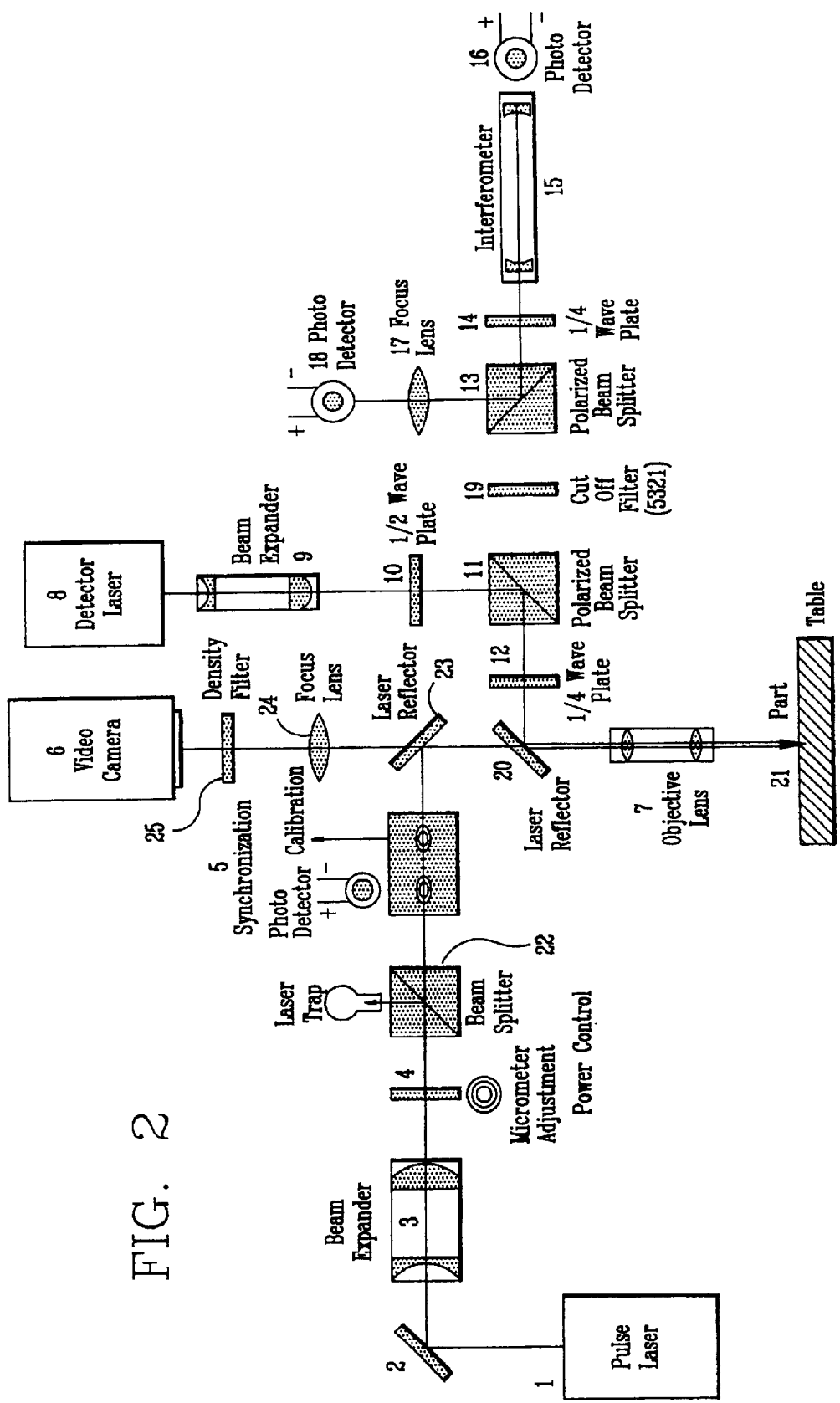
FIG. 2 is a schematic diagram of an optical system for evaluating bond integrity according to the present invention.

The two laser beams are applied through a complex optical system which is shown in schematic form in FIG. 2. This optical system has two main objectives. One is to direct and focus the pulse laser beam 110 to the intended target such as ball bonds, wedge bonds or interconnects. The second objective is to direct and focus the detector laser beam 112 to pick up the propagation waves generated by the pulse laser beam 110.

As illustrated in FIG. 2, the optical system of the preferred embodiment includes pulse laser 1, mirror 2, beam expander 3, power adjustment 4, beam splitter 22, synchronization photo detector 5, laser reflector 23, focus lens 24, density filter 25, video camera 6, laser reflector 20, objective lens 7, part table 21, quarter wave plate 12, polarized beam splitter 11, half wave plate 10, beam expander 9, detector laser 8, cutoff filter 19, polarized beam splitter 13, focus lens 17, photo detector 18, quarter wave plate 14, interferometer 15, and photodetector 16. The function of each of the components will now be explained in detail.

Pulse laser 1 is preferably a 1064 nm wavelength pulse laser with 10 nsec. pulse width (pulse duration) and pulse repetition rate of 100 Hz (100 times per second), is capable of delivering, for example, one Watt of energy. Since the wavelength of this pulse laser is the same as the detector laser, a frequency doubler was used to convert its useable wavelength to 532 nm and power to ½ watt. One appropriate laser is a Model #S10-5230 manufactured by Spectra-Physics. Other lasers could be used as long as they provide a similar high repetitive rate, short pulse duration, and consistency of pulse to pulse power levels. The laser should be selected to have a relatively low power because most higher powered lasers do not have high resolution in power control adjustment.

The pulse laser frequency preferably does not have the same frequency as the detector laser, so that the dispersed light is not interpreted by the photodetectors as false surface waves. The pulse width of the pulse is preferably short, such that the pulse is not continuing while the surface wave is already arriving at the detection point—especially when the distance between the pulse laser and the detector laser is in close proximity to each other and that the Rayleigh velocity for that material is fast—such as silicon etc. Ten nanoseconds is an appropriate pulse duration in typical micro-level applications. The pulse width of the pulse laser may be varied, thus changing the rate at which heat is applied to the pulsed surface. However, such variation typically changes the shape of the surface wave signature.

Surface mirror 2 is a surface reflector which receive the output of pulse laser 1 and redirects the pulse laser beam into beam expander 3. Of course, surface mirror 2 may be omitted if the laser is mounted horizontally.

Figure 3:
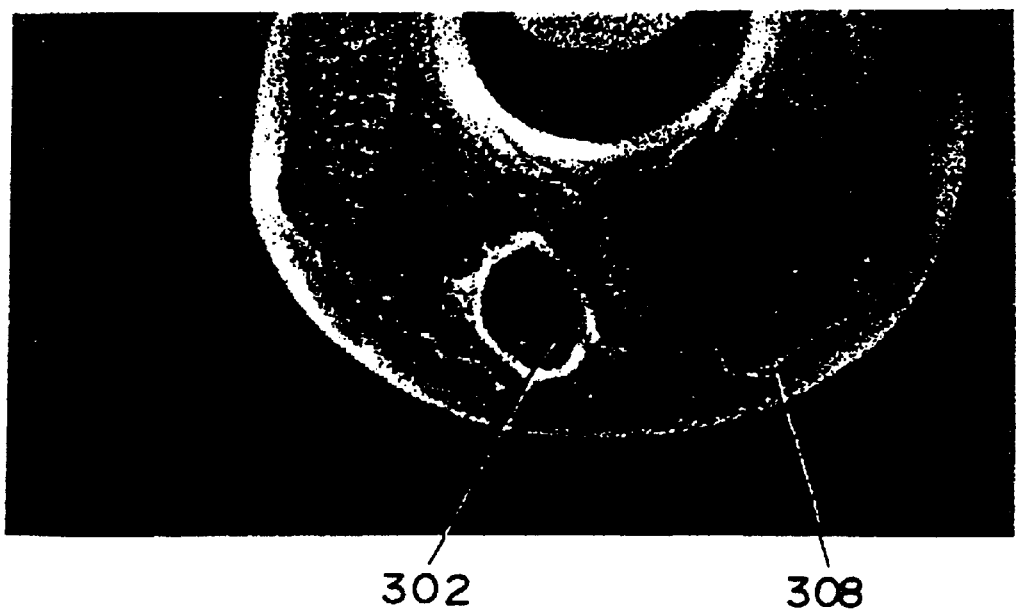
FIG. 3 is an illustration of a ball bond which has an ablated surface due to highly localized laser power application.

Beam expander 3 controls the collimation or divergence of the laser beam as it exits the pulse laser, to produce the desired beam (spot) size of the pulse laser when it reaches the point of interest (i.e. the ball bond, wedge bond and any other interconnects). The inventor has found that it is important to control the spot size of the pulse laser such that is appropriate to the size of the object being pulsed. In the case of a ball bond, the spot size of the pulse laser should be approximately the same size as the ball bond (0.003" in diameter), and preferably slightly larger than the ball bond. If the spot size is too small, the power density of the laser will ablate the surface materials. This ablation effect (vaporization of materials) will deposit undesirable metallic debris on the microcircuit. FIG. 3 shows a ball bond 108 with an ablated region 302 resulting from application of a highly focused laser pulse that is much smaller than the ball bond. Reducing the laser power will eliminate the ablation effect. However, reducing power also has the undesired effect of reducing the magnitude of the surface wavesignature which must be detected. Therefore, a balance between the pulse laser power and the spot size of the laser important for optimizing signature and minimizing any damaging effect on the materials being pulsed.

Figures 4A, 4B:
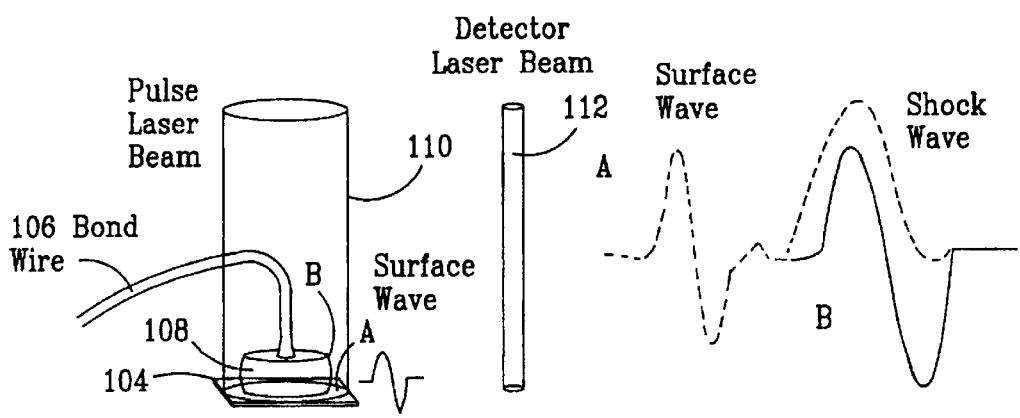
FIG. 4a is a view showing the application of a pulse laser beam spot much larger than a ball bond to be tested.
FIG. 4b is a graph showing the amplitudes of a resulting surface wave and shock wave, respectively.

Preferably the size of the pulse laser spot is slightly larger than the ball bond, and the laser power is adjusted so that no ablation occurs either on the ball bond or on the substrate areas adjacent to the ball bond. The possibility of increasing the pulse laser spot to a size much larger than the ball bond was also considered. While this approach may be used, it is less preferable because it has potential undesired side effects. In the illustration of FIG. 4, the pulse laser spot is much larger than the diameter of the ball bond. A significant amount of laser energy (1) "spills" over ball bond and is pulsing the surface to which the ball is bonded. This may damage the surface materials because they normally do not have as high a melting point as gold, thus ablation of material occurs. In addition, a surface wave is generated from the surface and will arrive at the detection point first. As long as there is no ablation of the surface, these two separate waves will arrive at different times—one from the surface (A) and the other from the top of the ball bond (B). This will still provide adequate distance between the two signatures for analysis. However, if ablation occurs on the substrate surface, the shock wave from the surface (A) will arrive approximately the same time as the wave from the ball bond (B), thus causing an overlapping of signatures. This invalidates the detection of the signature of interest resulting from application of heat to the top of the ball bond. Also, if the pulse spot size is excessively large, this will inhibit placement of the detection laser close to the pulse laser, and the increased distance between the pulse and detector laser will provide a weaker signature or poorer signal-to-noise ratio. The inventor's experience suggests that for microelectronics ball bonds, the spot size should typically be between 0.001" to 0.005" in diameter depending on the diameter of the ball bonds.

Figure 5:
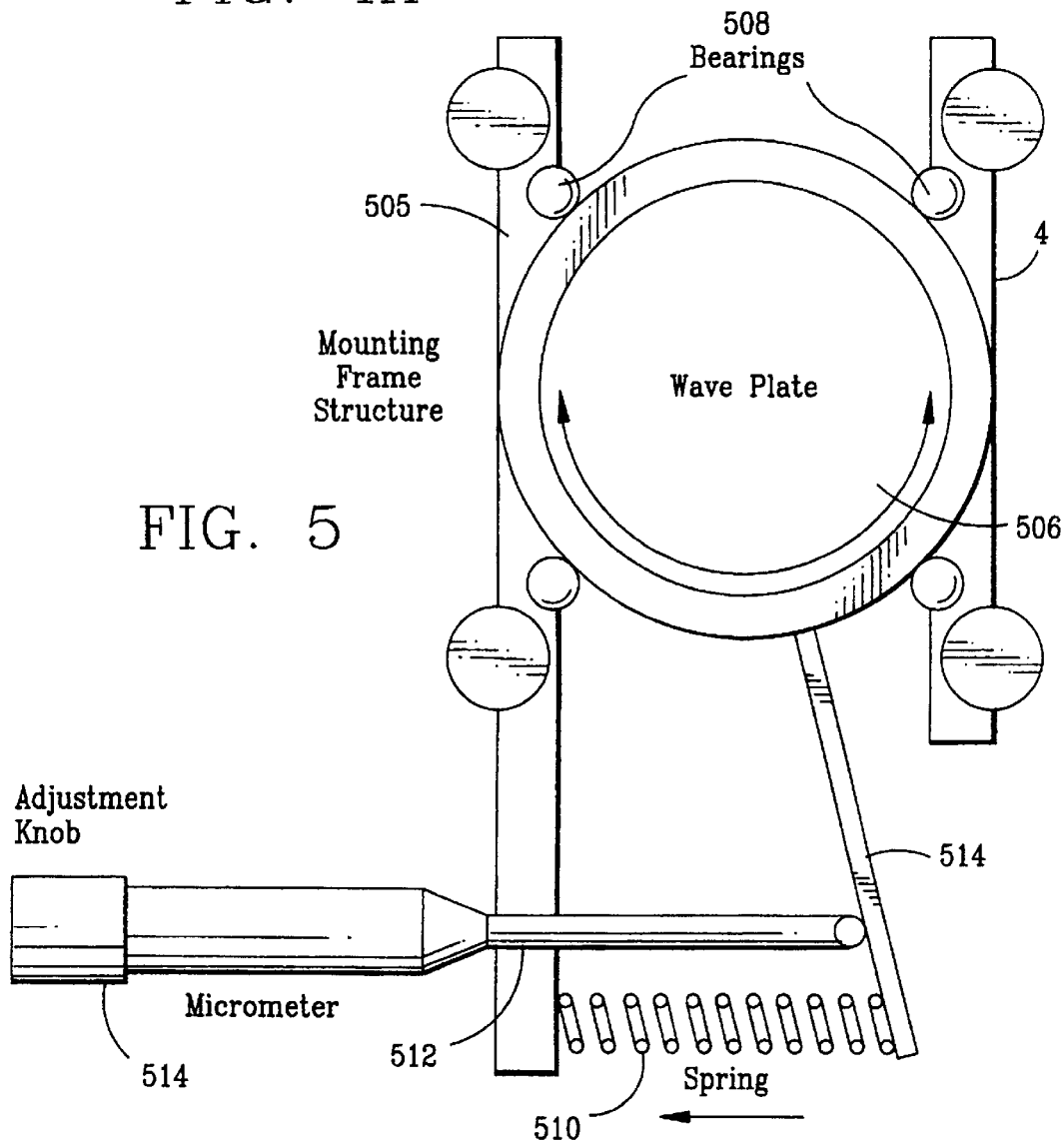
FIG. 5 is an end view of a preferred embodiment of a power control assembly according to the invention.

FIG. 5 shows the structure of a preferred embodiment of high resolution power control assembly 4, which is a means for finely adjusting the power transmitted by the pulse laser to the bonded item. This embodiment of high resolution power control assembly 4 comprises a half wave plate assembly 502, micrometer adjustment 504, a polarizing beam splitter cube 22, and a power trap 26 (shown in FIG. 2). Half wave plate assembly 502 comprises frame structure 505 which supports wave plate 506 via bearings 508. A spring 510 biases a lever 514 (attached to wave plate 506) against the screw 512 of micrometer 504. The function of assembly 4 is to provide much finer power control of the pulse laser than is provided by the power controls of a typical laser panel. As discussed above, the amount of power from the pulse laser must be well controlled to prevent material ablation. In this design, wave plate 506 may be rotated precisely in both clockwise and counter clockwise directions to establish a desired position, by adjusting the high precision micrometer. The rotational position of the wave plate will establish a polarization of the laser light which will interact with the polarization of beam splitter 22 (shown in FIG. 2) so that a variable percentage of the laser light power is passed through both wave plate 506 and beamsplitter 22. A 90 degree rotation of the wave plate will permit a full range of power (0 to 100%) to pass through. The use of the micrometer provides an infinite degree of power level control for the system. Due to the fine adjustment possible with micrometer 504 and the advantage provided by lever 514, it is possible to select a rotational position of wave plate 506, and thus a power throughput level, with great precision. This power control design can be used to accommodate different materials having different ablation tolerances. Laser trap 26 (shown in FIG. 2) is used to capture the residue laser power for safety reasons.

In addition to tight power control, a method for monitoring and calibrating pulse power during operation is also necessary. System synchronization and power calibration assembly 5 is preferably mounted in line with the pulse laser as illustrated in FIG. 6. A small piece of thin glass 602 (medical grade) is attached to the end of monitoring tubes 604 at an angle (45°) as illustrated in FIG. 6. As the laser pulse 110 passes through the thin glass 602, a very small amount of laser light is reflected 90° upward, while most of the light energy penetrates through glass 602. A high speed photodiode 606 is mounted permanently on the first monitoring window 608 to capture part of that reflected laser energy from the laser flash. The presence of this laser flash confirms to the system that the laser has indeed fired and that the laser pulse is on its way to the test surface. This confirmation flash initiates time (0) for the high speed transient recorder in a manner which will be described later in more detail. The second window 610 is for attaching a commercially available power meter 612 to perform periodic adjustment, calibration and verification of both the power control assembly 4 and the power monitoring (photodiode) devices.

Due to the short duration between pulse impact on the ball bond and the arrival of the surface wave to the detector (normally a 200 nanosecond window), synchronization of the data capture timing becomes an important part of the overall system design. Traditional computer control proved to be too slow and ineffective in synchronizing the time between laser triggering and start of data capturing. It is inherent in most pulse lasers that there is a variable delay between the time it receives a command to fire (trigger) and the time it actually fires. The time variance is normally in thousandths of a millisecond (0.001 seconds). The same order of magnitude of timing variation can be found in the response of a computer executing a laser triggering or data capturing command. Due to the close proximity between the pulse and detector beams on the test surface (approx. 0.005–0.010"), the useful surface wave duration is in the order of 200 nanoseconds (0.0000002 second). As illustrated in the timing chart of FIG. 7, inherent delays might easily cause data capture to be missed and make it difficult to determine whether the waveform observed is the waveform of interest from the ball bond, or a preceding surface wave.

This synchronization/power control design serves several purposes. The most important benefit from this design is the synchronization of data capture to the application of the pulse laser. As photodiode 606 senses a predetermined rise in voltage, which is a good indication that the pulse laser has fired and that its pulse is on its way to the top of the ball bond or interconnect, the data capture window is immediately activated or synchronized by the Analog to Digital (A/D) converter. This approach compensates for delay time in computer processing as well as inherent laser trigger delays.

In addition, this synchronization technique assures a consistent starting point for signal monitoring, capturing and averaging. This synchronization technique is important for supporting subsequent signal averaging methods for improving signal to noise ratio. A slight shift in time zero will null the surface wave propagation signals (using signal averaging methods), resulting in a much weaker reported signature than actual. Further, this technique provides a quantitative measurement of the output power (in millivolts) as the laser pulse travels through its path. This output power can be used to monitor the performance of the pulse laser.

As another feature, the amplitude of the output power can also be used to calibrate and normalize signature amplitude as part of the signature analysis equation.

It was observed that prior art attempts at laser bond integrity detection were primarily directed to larger objects such as a solder joint. The distance between the pulse and detector is further apart compared to micro-interconnects. The arrival time and signature duration is much longer as well. On the micro scale, the present invention operates with a distance between the pulse and detector laser spots which is much closer, resulting in a shorter arrival time. Therefore the synchronization requirement for the present invention is much more significant than in prior art systems.

Referring again to FIG. 2, a commercial off-the-shelf color camera 6 is used for targeting and viewing of the material under test. The in-line laser reflectors, focus lens and objective allows the viewing and focusing of the camera, the pulse and detector lasers onto the material being tested. A density filter can be used to filter out unnecessary glare from both the detector and pulse lasers. This video camera is connected to a vision system for determining the target locations.

A common objective lens 7 magnifies the field of view for the pulse laser, detector, and video camera. Since the materials being tested are small (balls, wedges and interconnects), the field of view has to be magnified. Because of the dimensions involved, it is difficult to provide the pulse laser, detector and video camera with their own respective optical paths, so in the preferred embodiment a common objective lens accommodates all three systems.

The reflection of detector laser 8 is used to monitor vibrations propagating through the substrate following the application of the pulse laser. The detector laser is preferably a stabilized, single frequency laser, with continuous wave (CW) of 1064 wavelength. Since the bond integrity information is imbedded as part of the return (reflected) beam, the amplitude is, therefore, dependent on the reflectivity of the material surface and the power level of the detector laser. Preferably, the detector laser power may be set at approximately 700 milliwatt to optimize the signal-to-noise ratio. The inventor has tested the system using lower detector power levels (i.e. 15, 40 and 500 milliwatt respectively), but with limited success. The advantage of high detector laser power is a higher amplitude return signal, but additional laser power may also deposit excessive heat to the test surface. A balance between these competing concerns must be struck based on the nature of the materials under test.

Beam expander 9 controls the collimation or divergence of the laser beam as it exits detector laser 8. This beam expander is necessary to control the beam (spot) size of the pulse laser when it reaches the point of interest (i.e. the surface of the test material). As for the spot size of the detector, will provide best results when the beam is small and focused. However, the high power density vs. signal amplitude, discussed above must be considered.

Figure 8:
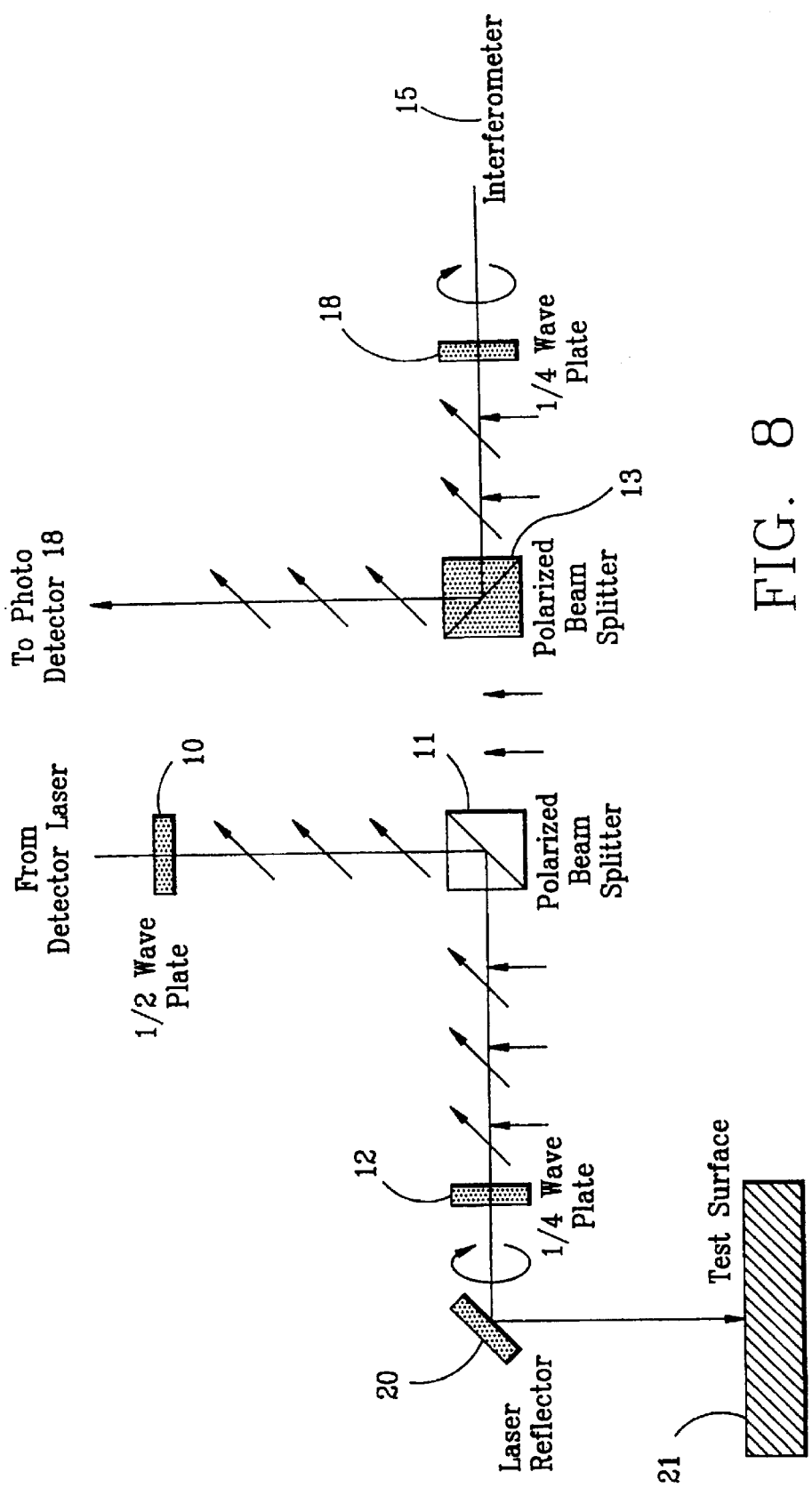
FIG. 8 is an optical schematic diagram showing details of the detector laser transmission and reflection detection optics.

A set of wave plates and polarized beam splitters 10, 11, 12, 13, and 14 are used to control the amplitude and flow of the laser beam from exit of detector laser 8 to the return beam at photodiode 18. The arrangement of the wave plates and the polarization of the laser beam as it travels through the system is illustrated in more detail in FIG. 8.

As the laser beam exits detector laser 8 (shown in FIG. 2), it travels through the first half wave plate 10 which polarizes the beam to horizontal orientation. Polarizing beam splitter 11 reflects the horizontally polarized beam towards the quarter wave plate. As the beam travels through the ¼ wave plate, it is reflected onto test surface 21 through objective lens 7 (shown in FIG. 2) by laser reflector 20. The beam is then reflected from the test surface 21 and laser reflector 20 back through quarter wave plate 12. At this time the polarization of the beam is rotated 90° from its entry orientation, to vertical polarization. The vertically polarized beam will travel through beam splitters 11 and 13 and quarter wave plate 11. As the beam returns from interferometer 15, quarter wave plate 11 will rotate the polarization of the beam 90° from its entry orientation, in this case, to horizontal. The beam is then reflected from polarizing beam splitter 13 through focus lens 17 (shown in FIG. 2) onto photo detector 18.

Focus lens 17 focuses the beam onto the center of photo detector 18. Besides manipulating the polarity of the beam, half wave plate 10 is also used to control the power level of the detector laser beam prior to entering the test sample. Only the horizontally polarized portion of the beam is reflected to the test surface while the vertically polarized portion of the beam will go through polarized beam splitter 11 and is captured by a laser trap for safety reasons. Rotating half wave plate 10 will divert desired portions of the beam to the appropriate direction.

A Fabry-Perot interferometer 15 is used in the preferred embodiment, with 93% reflectors used inside the interferometer. Selection of these reflectors will provide analog responses from the detected surface displacements. Other interferometers having similar performance, such as Homodyne interferometer, can also be used for this application.

Figure 9A:
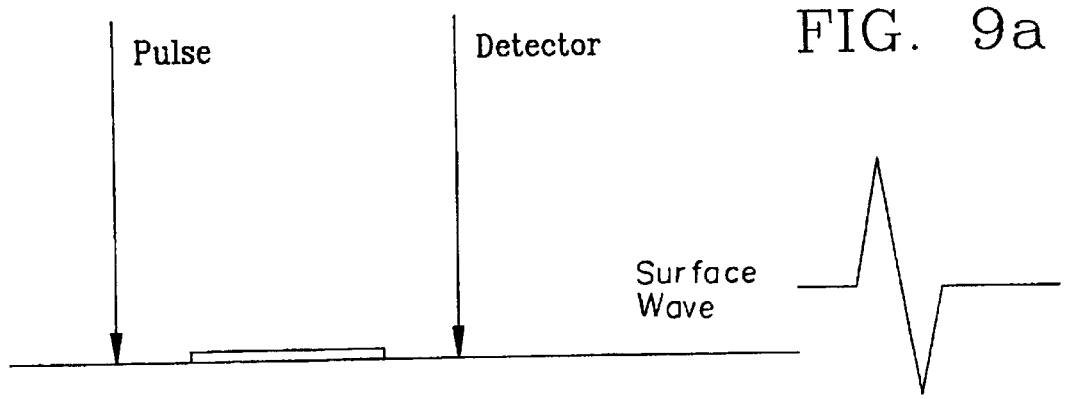
FIGS. 9a and 9b are side views showing an alternative embodiment of the invention wherein bond integrity is detected by applying a laser pulse adjacent to a bond and detecting the resulting surface wave on the substrate on the other side of the bond.
Figure 9B:
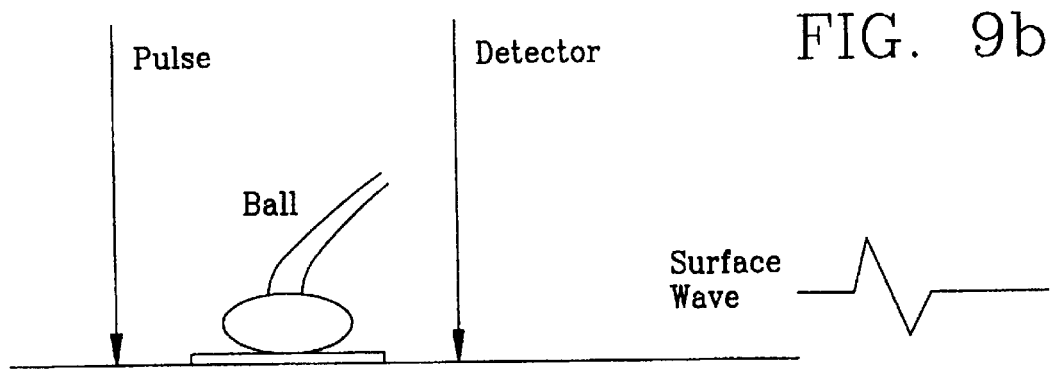

Referring again to FIG. 1, normally the ball bonds, wedge bonds and interconnects are pulsed by the pulse laser and the detection is performed at the neighboring surface. It has been found that it is possible to pulse the material on one side of the ball bond and detect on the same surface on the opposite side of the ball bond. FIGS. 9a and 9b illustrate this alternative test technique in which pulsing and detecting occur on the same material surface and on the opposite side of the interconnect. The resultant signature differs from the first embodiment discussed above (i.e. pulsing the ball and detecting on the surface). Instead of looking for a positive wave form caused by the joining surfaces (intermetallics), this technique detects the dampening effect caused by the bonded mass of the ball bond, wedge bond or the interconnect.

As illustrated in FIG. 9a, a surface wave will be detected without the presence of a ball bond. On the other hand, when a ball bond is situated between the pulse and detector, a dampening effect, or a weaker signature can be detected as shown in FIG. 9b. Depending on the bond integrity of the ball bonds, a different degree of amplitude and wave form is experienced. For a well bonded ball, the surface wave is diminished. For a non-attached but contact bond, the surface wave stayed intact or undisturbed. By correlating the change of amplitude and wave forms, varying degree of bonding for interconnects (ball bonds, wedge bonds, solder bonds and interconnects) can be determined at high speed.

This alternative embodiment has many advantages over previously known test methods. First, the pulse laser need not contact the interconnect other than its neighboring surface. This is especially important where the interconnect is extremely fragile or sensitive to heat generated by the pulse laser. Also, the arrival time is much faster than previous techniques because the surface propagation travels only over the surface between the pulse and detector laser beams. It does not have to travel from the top of the ball bond to the surface of the substrate. Depending on the size of the ball, the travel time ranges from 55 to 70 nanoseconds.

The most important benefit of this technique is that the wave form is much simpler for correlation. In this case, the waveform is not affected by the shape of the bond wire protruding from the top of the ball bond. The resultant waveform normally takes the general form of the surface wave. Also, the spot size of the pulse laser is not limited by the size of the ball bond, wedge bond or other interconnect.

This technique is most effective when the detector beam is positioned close to the interconnect. The pulse laser, however, does not have to be close to the interconnect for effective results. One caution in using this technique is that, in the event that the surface material is sensitive to the heat generated by the pulse laser, a larger pulse spot (such as line shape pulse laser) should be used to prevent material ablation. A larger pulse spot with the same power setting will reduce power density on the surface of the test materials, thus eliminating ablation effects.

Concentric detection techniques which are also useful in some embodiments of the present invention will now be described in more detail.

Figure 10:
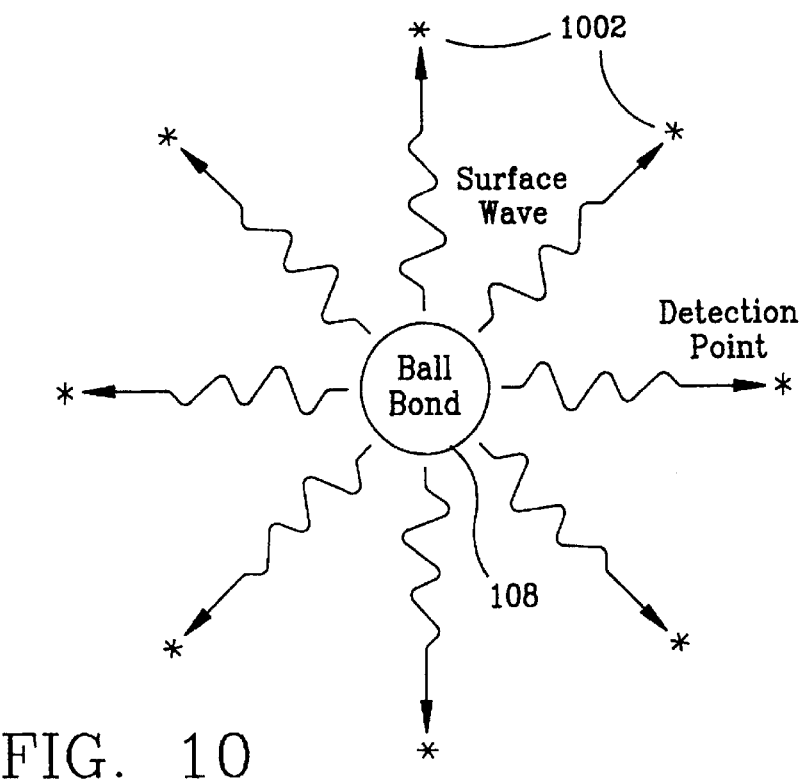
FIG. 10 is a top view of a ball bond showing another alternative embodiment in which the intermetallic structure of a bond is analyzed by collecting vibration propagation data at a plurality of points around the bond.

Due to the sensitivity of the integrity detection according to the invention, it has been found that the surface wave propagation corresponds directly to the structural configuration of the joining intermetallic. Since most joining intermetallics are not perfectly uniform, the surface wave propagations radiating from the center of a ball bond are not uniformly concentric either. By capturing multiple signatures from different positions around the ball bond, sequentially or concurrently, the structure of the joining intermetallic can be deduced. FIG. 10 illustrates the pulsing and detection technique for determining the intermetallic structure using laser ultrasonic techniques. The ball 108 is pulsed from the top and detection is performed on the joining surface, 360° around the ball at a plurality of locations 1002. To avoid the need for a plurality of detection lasers, optics, and data processing systems, a single detection apparatus may be used sequentially to obtain waveform data for each of the plurality of locations 1002. For example, a ball bond is placed on the concentric center of a rotary table prior to initiating testing. A detector beam is positioned at a predetermined distance from the center of the ball, say 0.006". A pulse (or a series of pulses) is directed onto the top of the ball bond, radiating surface waves outwardly from the center of the ball. The detector picks up the surface waves and is printed or stored. The ball bond is then rotated by turning the rotary table at a predetermined angle, say 5 degrees. A second pulse or series of pulses are initiated and the signature(s) detected and stored. The process is repeated until signatures at all points 1002 around the ball bond are collected. The distance between detector points depends on the radial resolution desired.

Once these signatures are collected, they can be displayed in 3-D format, thus providing the propagation "view" of the intermetallic structure. This format can be correlated or interpreted to the structure of the joint and displayed for viewing.

The laser trigger control in the present invention is part of a system control design which monitors the status (sensitivity positions) of the Bond Integrity Tester, and initiates the triggering of the laser (or initiates the test). This trigger control compensates for the inherent wavelength ($\lambda$) drift of the detector laser beam as well as the mirror positions inside the interferometer. System performance and sensitivity to surface propagations are directly affected by these drifting problems. In other words, if tests are performed at the precise optimal system sensitivity, strong signatures will result for analysis. On the other hand, if the tests were performed when the wavelength shifted slightly or the mirror positions have drifted off its pre-set positions, signatures received will be weak or even non-detectable. These drifting effects are amplified when signal averaging techniques are employed. To overcome the above mentioned problems and assure consistent test results, two techniques have been developed, which will be referenced as the Static and Dynamic Triggering Control Modes, respectively.

Figure 11:
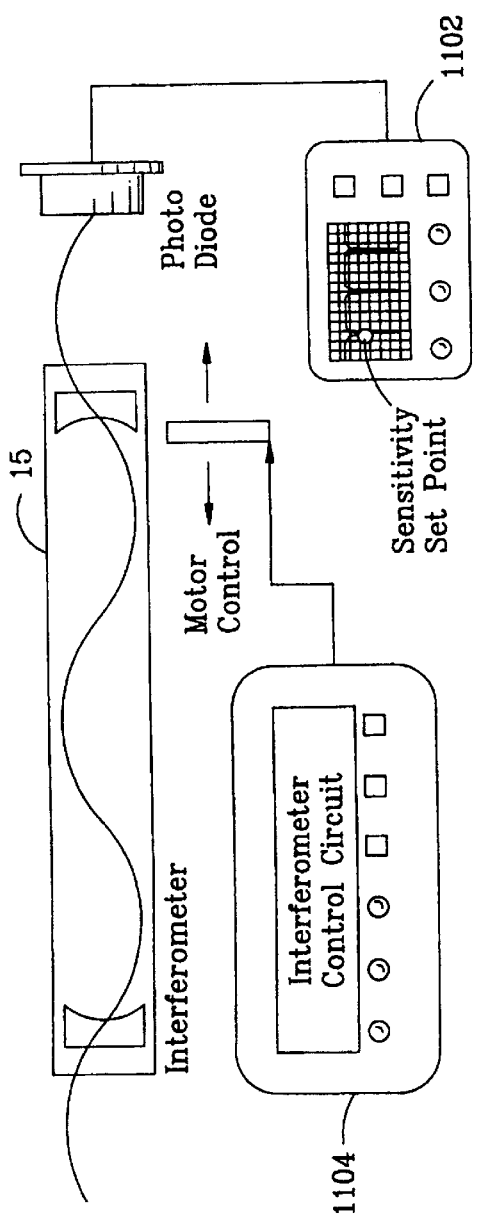
FIG. 11 is a diagram showing the operation of the invention's static mode for setting sensitivity of the interferometric circuit.

The static control trigger mode is used primarily for manual testing where the user can view and set the laser trigger point prior to each test. As illustrated in FIG. 11, a circuit monitors the amplitude (voltage output) of photodetector 16 from the interferometer 15 and provides feedback through an analog oscilloscope 1102. This feedback provides a reference between the laser triggering point and the actual optimal sensitivity of the system. The user has the option to re-set the trigger point at any sensitivity level of the system (i.e. most sensitive, least sensitive, or anywhere in between) prior to triggering the laser. This setting is accomplished by adjusting the distance between the reflective mirrors inside the interferometer cavity to accommodate the drifting effect discussed above. Operation of this Static Trigger Control Mode is accomplished by adjusting a knob at the interferometer mirror controller 1104 while observing the photodiode feedback. Once the trigger point is set, the user can initiate the firing of the trigger. This mode is especially useful for single pulse testing and system calibration. The drawback of this mode is that accommodation for drift is manual and therefore more time consuming. However, the user has the freedom to set the laser trigger point anywhere along the sensitivity range of the system, for investigative and calibration purposes.

Figure 12:
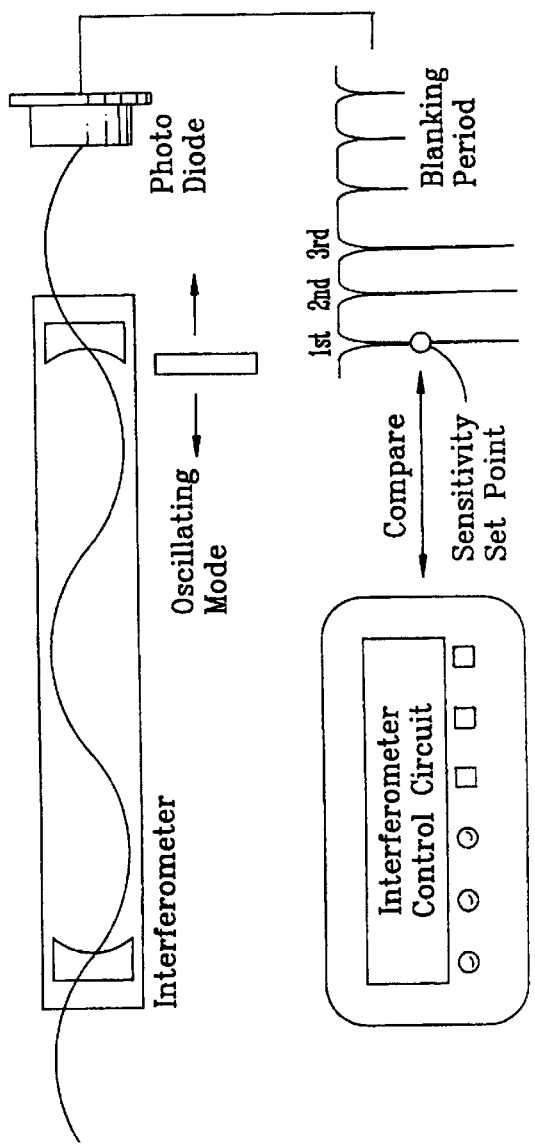
FIG. 12 is a diagram showing the operation of the invention's dynamic mode for setting the sensitivity of the interferometric circuit.

The dynamic trigger control mode is optimized for automatic testing at high speed with simultaneous adjustment to sensitivity drift. In this mode, the mirror inside the interferometer is set at a continuous scan (oscillating) mode such that multiple photo peaks can be observed (i.e. the interferometer mirror is made to travel a distance of several wavelengths of the detector laser frequency and return). For example, the distance may be set at 3 photo peaks—regardless of frequency drift, the system will cross over six (6) optimal sensitivity points (3 one way and 3 return). As illustrated in FIG. 12, a circuit monitors the returned peaks (blanking periods) and especially the first ($1^{st}$) peak after the blanking period. The circuit also has a comparator circuit to compare the voltage amplitude from the $1^{st}$ photo peak (as it is scanned) against a pre-determined voltage value stored in its PROM. Once these two voltage values match, the circuit initiates a laser trigger command to the laser. The voltage value stored in the PROM is preferably a value that will be achieved at time Tf before the optimal photo peak., where Tf is an average time between transmission of a signal to fire the pulse laser, and the actual firing of the pulse laser.

The Dynamic Trigger Control Mode circuit performs continuous triggering and keeps track of the number of triggers for each session. Once the trigger command equals the trigger count value stored in the PROM, the trigger session ends. Both the trigger count value and the pre-determined voltage amplitude in the PROM are input from the system control computer prior to each test session.

Since the interferometer control system of the present invention supports a scanning rate of 100+ cycles per second, testing of joints at optimal sensitivity can, therefore, be performed in excess of 100 points per second as well. This triggering control technique supports high speed testing with automatic accommodation to sensitivity drifts in the system.

The Dynamic Trigger Control Mode has many advantages. This mode adapts to inherent sensitivity drifts in the system automatically, supports computer controlled automatic testing (PROM inputs for count & sensitivity criteria), assures integrity tests at optimal system sensitivity (or any other pre-set sensitivity) from the PROM, supports high speed testing, and tracks single or multiple tests automatically.

A number of techniques are used in the present invention to improve signal to noise ratios. Signal-to-noise has always been a challenge to all electronics systems. This Non-Contact Bond Integrity Technology is no exception. In order to acquire the minute surface propagations generated at the bond, our detector sensor must be extremely sensitivity. Beside acquiring the surface propagation waves, other environmental noise such as Q-switch RF noise and ground noise are being picked up as well. The amplitude of these noises, at times, are greater than those of the propagation signatures. Since most environmental noise is random, while our surface wave is fixed, a signal averaging technique is used to cancel out these unwanted noises.

Beside signal averaging techniques, other considerations for increasing the amplitude of the signatures are desirable. The most significant implementation issues are careful selection of appropriate photodiodes, increased detector laser power, and reduced detector laser spot size.

Figure 13:
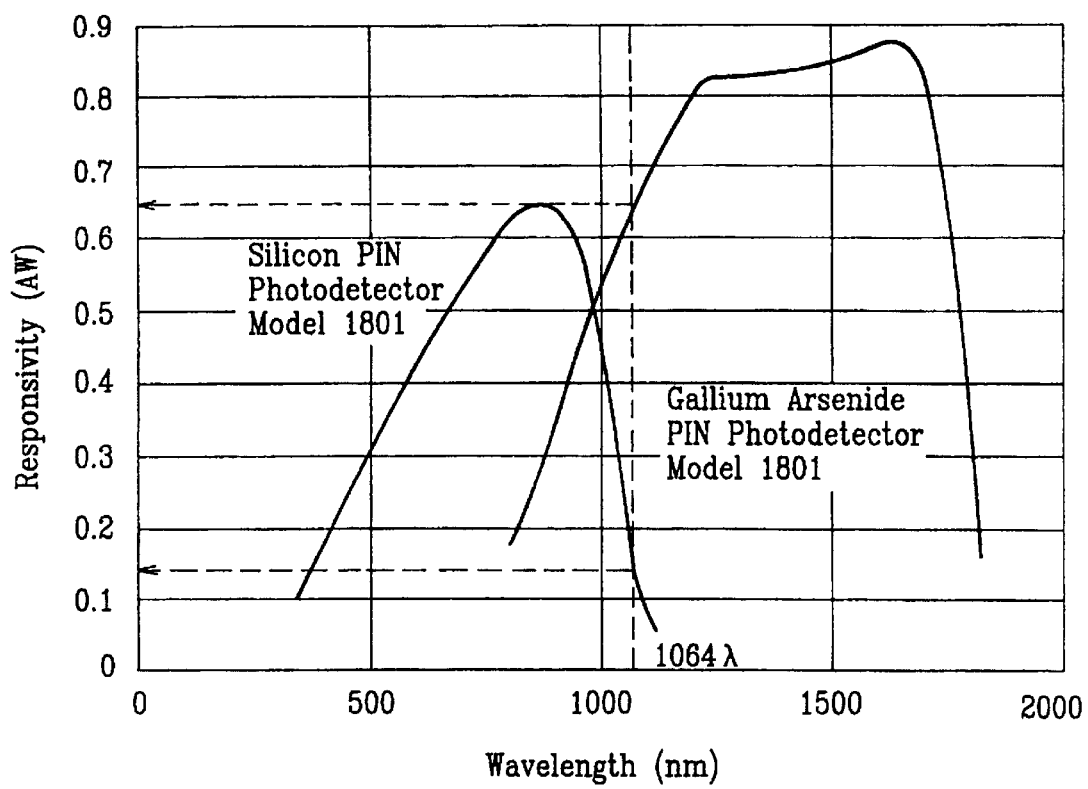
FIG. 13 is a graph comparing responsivity of a silicon PIN photodetector to a Gallium Arsenide PIN photodetector for various wavelengths.

Photodiodes that were supplied by the interferometer manufacturers used silicon based photodiodes. It was found that system operation is improved by substituting photodiodes that are more responsive to the preferred detector laser frequency of A $\lambda$=1064 nm. As illustrated in FIG. 13, gallium arsenide photodiodes are approximately 4.3 times more responsive to the preferred detector laser frequency. This equates to in excess of a 400% improvement in signal-to-noise ratio.

The amplitude of the return signature is dependent on the amount of light reflected from the test surfaces. Due to the tremendous loss of light energy through the optics layers, the returned light energy is substantially attenuated. An increase of input detector laser power from 15 mW (as disclosed in the inventor's prior patent) to 700 mW was implemented and the signal-to-noise ratio was increased many times.

It was also found that minimizing the spot size of the detector laser increased the signature amplitude. Detector spot size was reduced to 0.003" in diameter for an improved signal-to-noise ratio.

Figure 14:
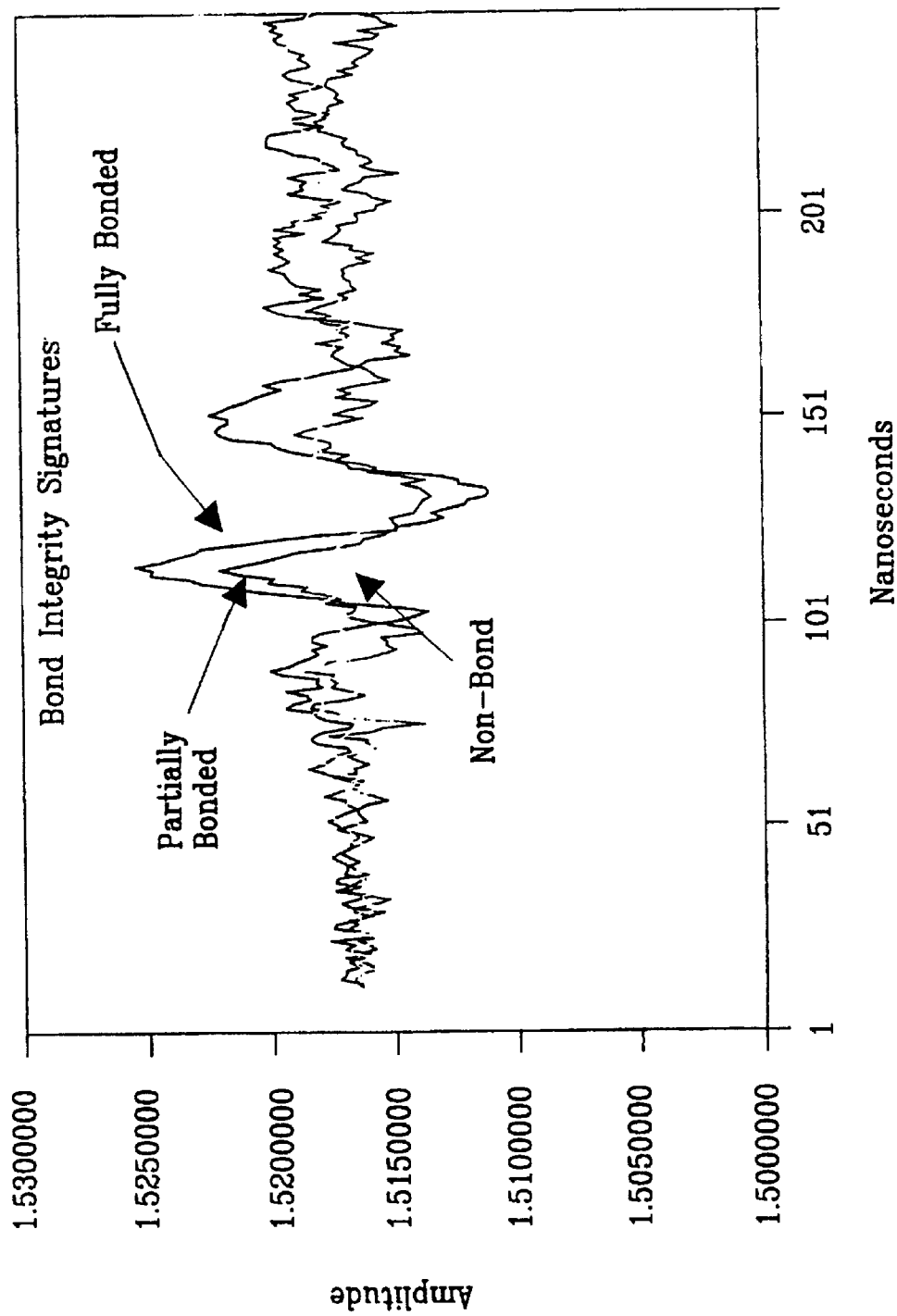
FIG. 14 is a graph showing sample bond integrity signatures for non-bonded, partially bonded, and fully bonded cases respectively.

Data collected using the present invention has substantiated that integrity of micro dimensioned material bonds can be determined using non-contact laser ultrasonic means. A surface wave signature generated by the above process is captured by an Analog to Digital converter operating at 500 MHz (i.e. 500 million samples per second). Preferably, 500 data points are collected for each signature at 2 nanoseconds per point. FIG. 14 shows signatures for a well bonded ball bond, a partially bonded ball and a non-bonded (touching) ball. Note that the design of the present invention eliminates shock waves that were present in the signatures in the inventor's prior U.S. Pat. No. 5,535,006.

Figure 15:
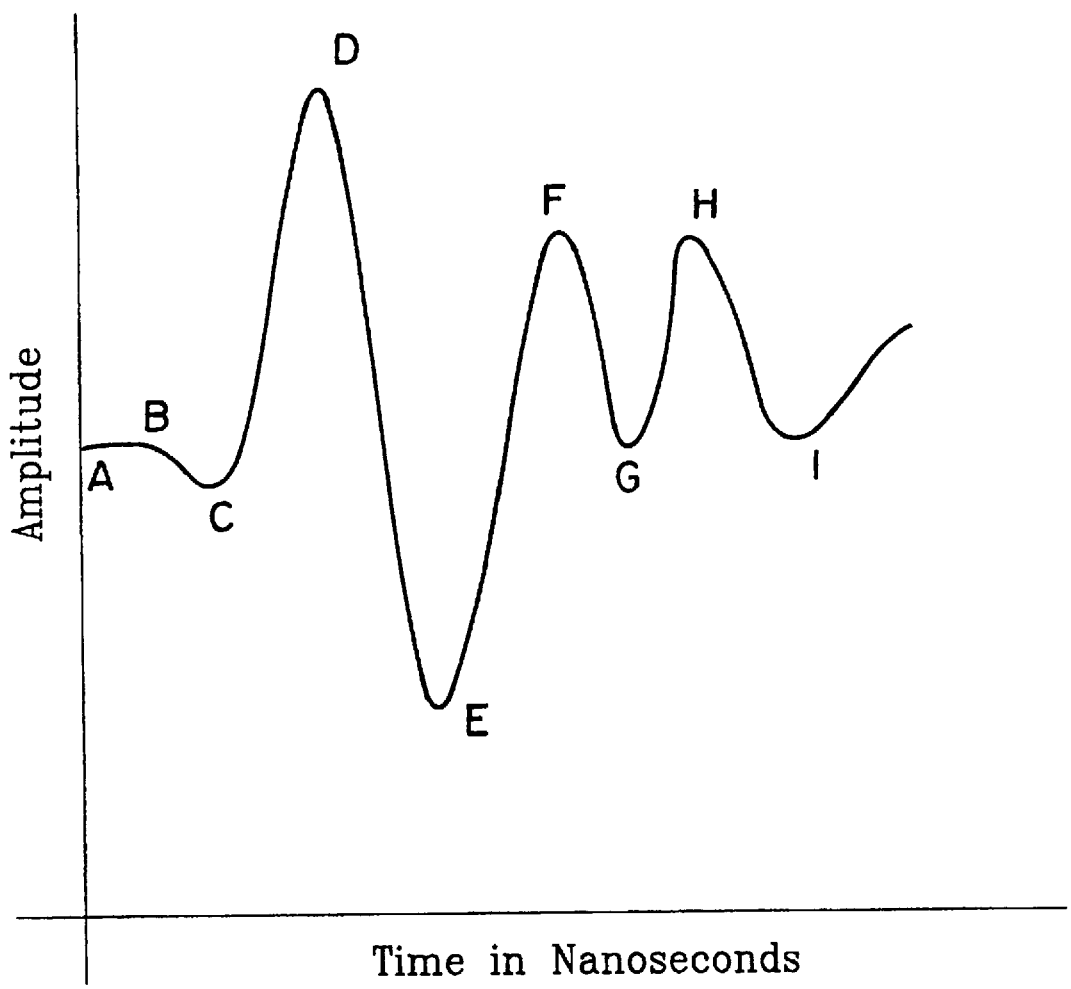
FIG. 15 is a simplified bond integrity signature diagram showing key analysis points for the waveform.

In the preferred embodiment, only the early segment of the signature is used for correlation because surface waves rebounding from its neighboring bonds (structures) may arrive at the detection point, thus resulting in a complex signature. Besides amplitude of the spikes, several features of the signature are used for bond integrity correlation. The combination of these features (seed parameters) provides a much better distinction between a good, partial and non-bond. FIG. 15 shows a sample signature which will now be referenced in explaining elements of the signature analysis used in the present invention.

The arrival time of the first surface wave spike (Point C in FIG. 15) is detected to assure that the system is performing as expected because the surface wave, regardless of its bond integrity, should travel at the same velocity. Abnormal arrival time normally indicates unusual bond structures or interconnect features. The arrival time of a surface wave is dependent on the materials being used, the Rayleigh velocity and the distance between the pulse and detector laser spots.

The vertical separation between Pt. C and Pt. E as shown in FIG. 15 increases as the shear force increases (or as the bond integrity improves) calculating the vertical distance between the two points. The distance is an indicator of bond integrity and is used as one of the seed parameters for predicting bond status of the interconnect.

The slope between Pt. D and Pt. E correlates closely with shear strength. Our data analysis software routine identifies the Maximum point (Pt. D) and Minimum point (Pt. E) within a pre-determined time window automatically and performs a regression analysis with all the data points in between. The slope of this regression analysis corresponds directly to the bond integrity of the interconnect. The steeper the slope, the stronger the bond is experienced. Conversely, as the slope decreases, the weaker the bond forces.

Frequency, in this application, can be translated into arrival time of peaks and valleys of the $2^{nd}$ and $3^{rd}$ spikes. Among the 4 points (F, G, H and I), arrival time of Pt. I was used as a preliminary seed parameter. It is because Pt. I is the furthest point out in time and allows for better time separation among signatures of varying degrees of bonding. Empirical test data supports the above analysis.

Figure 16:
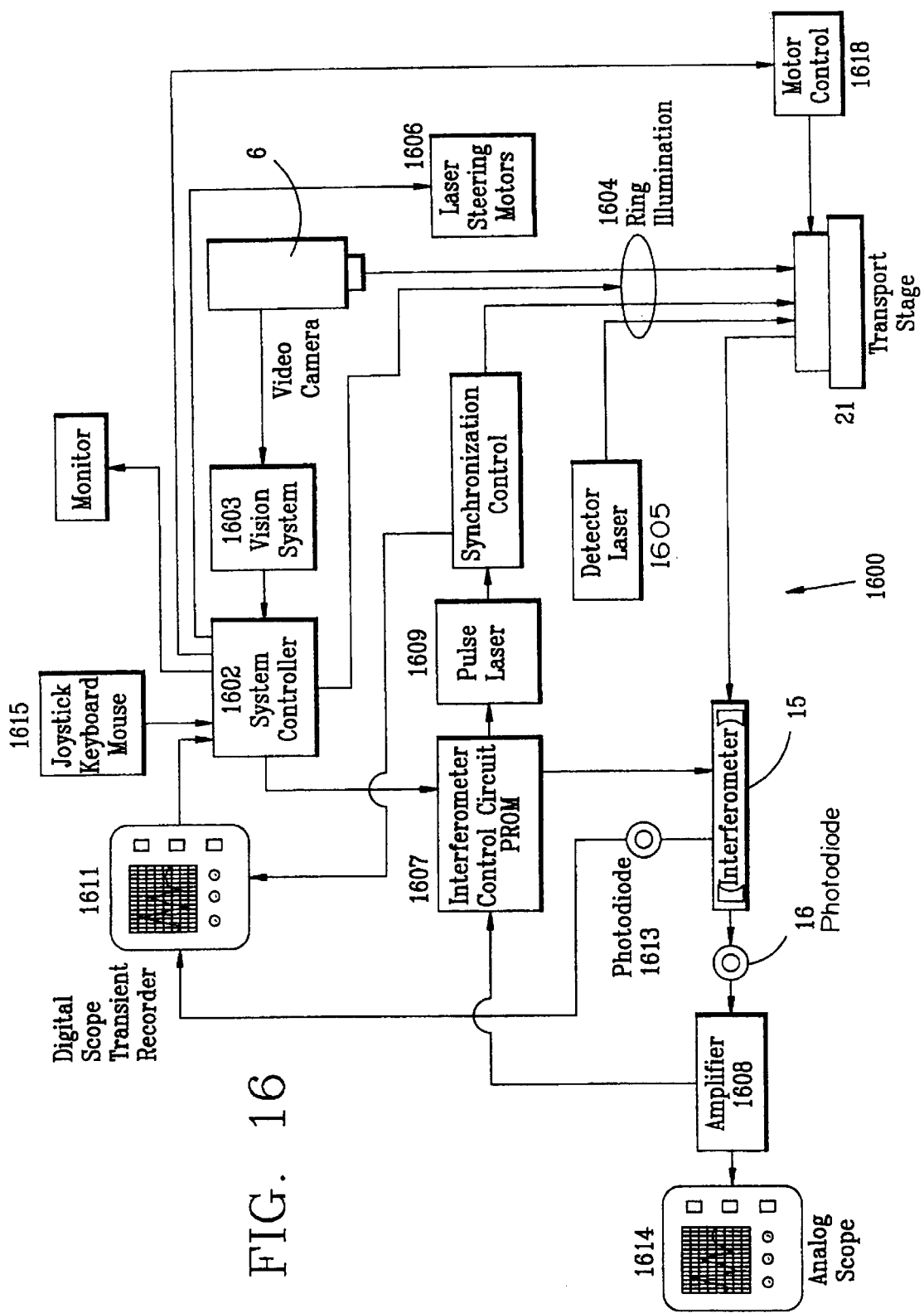
FIG. 16 is a schematic diagram of a preferred embodiment of the signature analysis system according to the invention.

FIG. 16 is a schematic diagram of a preferred embodiment of a complete inspection system according to the present invention. The system 1600 comprises system controller 1602, vision system 1603, ring illumination 1604, detector laser subsystem 1605, laser steering motors 1606, interferometer control circuit 1607, amplifier 1608, pulse laser subsystem 1609, synchronization control 1610, digital scope transient recorder 1611, photodiode 1613, analog scope 1614, input devices 1615, motor control 1618, interferometer 15, photodiode 16, and video camera 6. Pulse laser subsystem 1609 and detector laser subsystem 1605 are preferably constructed according to the description above and particularly with reference to FIG. 2. It will be apparent to those skilled in the art that much of the apparatus of FIG. 2 has been omitted from FIG. 16 for clarity, but that the same elements are preferably incorporated in the complete system of FIG. 16.

Figure 17:
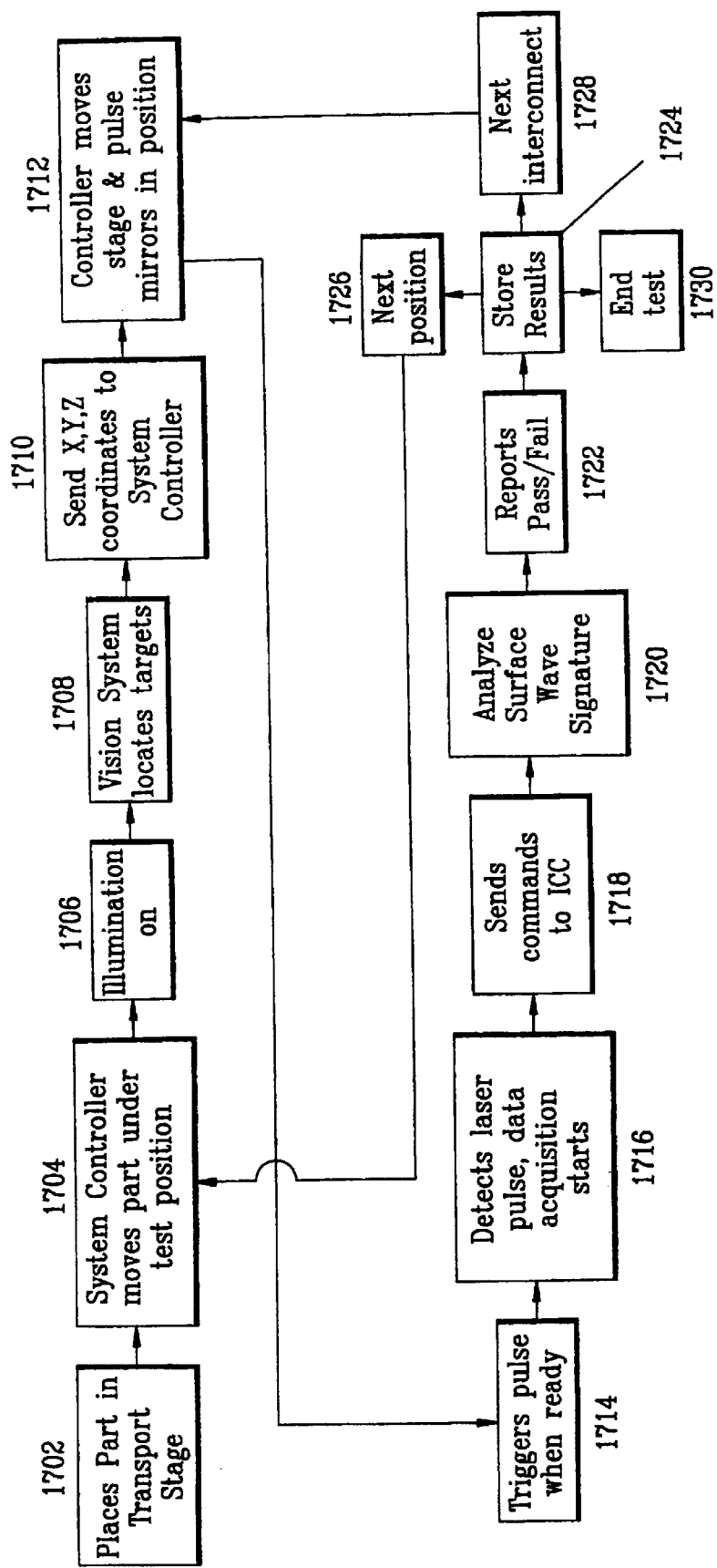
FIG. 17 is a flowchart showing the operation of an automated bond integrity testing process.

A functional flowchart showing a preferred embodiment of an automated test process is provided in FIG. 17. To start the test process, as shown in Block 1702, the operator places the part to be tested on the table 21, which in this embodiment is equipped with motors to translate it along two axes to form a transport stage. Next, in Block 1704, system controller 1602 moves the part under the vision system 1603 which controls part alignment and positioning. Then in Block 1706, the system controller energizes the ring illumination mechanisms 1604 to highlight the ball bonds and wedge bonds within the field of view. The ring illumination mechanisms and additional operating features of the system are preferably constructed according to the disclosures of the inventor's prior U.S. Pat. Nos. 5,420,689; 5,424,838; and 5,302,836, the disclosures of which are incorporated herein by reference. In block 1708, vision system 1603 identifies and locates the ball bonds, wedge bonds or interconnects to be inspected, and in Block 1710 it sends target coordinates to system controller 1602. System controller 1602 performs positioning modification using the transport stage 21 for the detector laser subsystem 1605 as well as the pulse laser steering mirrors 1606 for pulse laser targeting, as shown in Block 1712. System controller 1602 then sends a command to interferometer control circuit 1607 to perform the integrity test. The command, consisting of number of pulses and sensitivity level set point for laser triggering, are stored in the PROM of the ICC 1607.

Next, in Block 1714, ICC 1607 monitors the system sensitivity status via the amplifier 1608 and triggers the pulse laser subsystem 1609 at an appropriate time for predicted maximum sensitivity, given the expected time lag between transmitting the signal and firing of the laser. Once triggered, the laser pulse passes through the synchronization control unit 1610 which in turn, initiates the data capture function of the transient recorder 1611, as shown in Block 1716. The surface wave signature is captured and converted to voltage via the Interferometer 15 and photodiode 16 in Block 1718 and the signature is recorded by the high speed transient recorder 1611 for display. Subsequently, this data is also sent to the system controller 1602 for automated bond integrity analysis (see Block 1720). Results of the test are then displayed (Block 1722). Results are preferably stored for further review, analysis, and correlation (Block 1724). Depending on requirements for the automated test, control passes either to Block 1726 (where the next part is to be inspected), Block 1728 (where the part must be moved to test the next interconnect), or Block 1730 (where the test is complete).

The analog scope 1614 is provided for visual reference when static mode trigger operations are performed (as described above). The input elements 1615 may include a joystick, keyboard and mouse to enhance usability of the operating software.

In a preferred embodiment, the two oscilloscopes are implemented virtually in a single computer screen display, along with live video from video camera 6 for targeting purposes, on-screen mouse driven focus controls for video camera 6, and on-screen mouse driven controls for rotating and translating the transport stage.

In addition to evaluation the integrity of small bond areas such as ball bonds, the techniques and systems disclosed herein can be used to test bonding integrity in various other micro level applications. In particular, the invention can be used to test bond integrity in larger areas such as in thin coating. A good example of this application is detection of the presence and absence of voids, non-bonds but in contact, partial bond and fully bond conditions. Due to the thin coating of the material (on the order of microns), power density may be too strong if a spot pulse laser is applied. To overcome this potential problem, the preferred embodiment of this application uses an alternative optics design which decreases power density on the surface, yet maintains a high signal-to-noise ratio. Signature characterization relating to thin coating was addressed. A mathematical model is developed for each application (for example, a model for evaluating thin aluminium coating on silicon and correlating to actual signatures acquired by the system is described in more detail below).

Ablation may occur due to high density of energy being focused on the surface to create the propagation or surface wave. The inventor has determined that, power intensity of the pulse is directly proportional to the amplitude of the signature. In other words, the higher the pulse intensity, the stronger the pulse—thus a more recognizable signature. On the other hand, to reduce ablation effects, the lower the intensity of the pulse, the weaker the signature—thus decreasing the signal-to-noise ratio.

Figure 18:
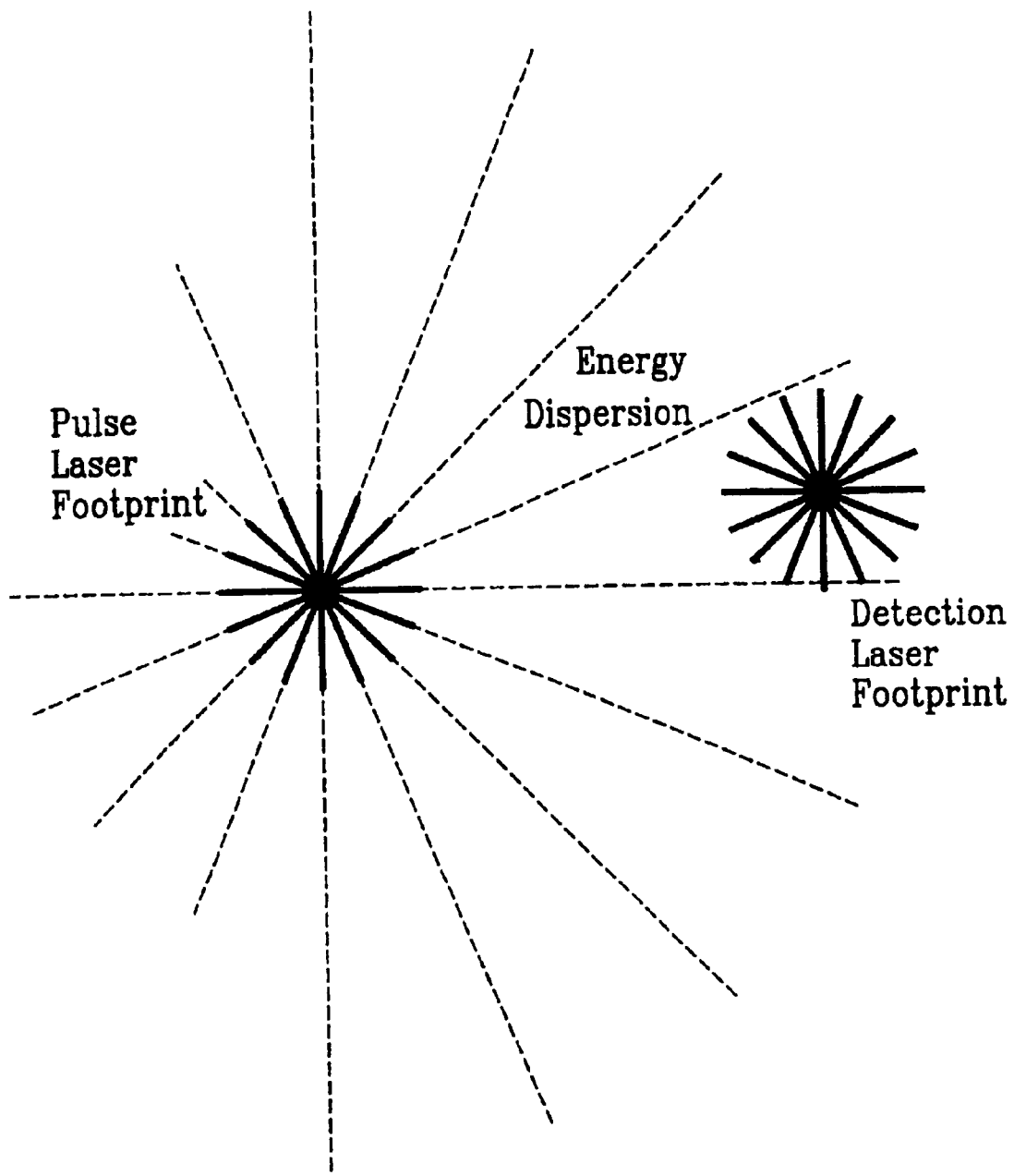
FIG. 18 is a top view showing energy dispersion of single pulse laser and detector laser footprints.
Figure 19:
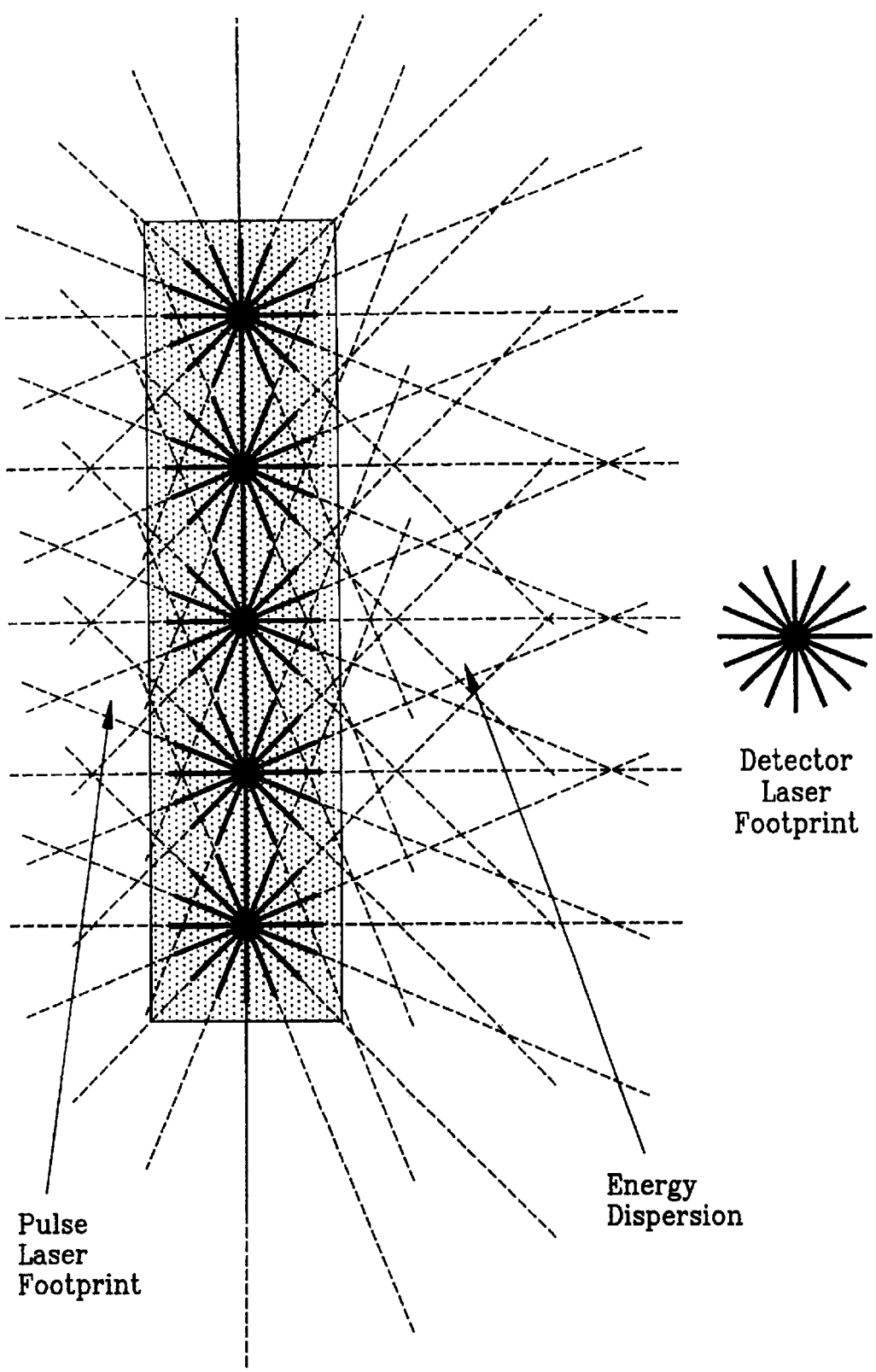
FIG. 19 is a top view showing energy dispersion of a wide or multiple pulse laser footprint used in an alternative embodiment.

A significant consideration in system design is maintaining the non-destructive nature of the sensor. If pulse laser beam is focused in a small spot, a large amount of energy (Mwatts) can be deposited onto the sample surface in a short time (nsec), causing material ablation. By modifying the optics design, an elongated pulse laser spot was provided for this embodiment. The elongated laser foot print reduces the power density on the surface materials, thus allowing a higher total input power to the surface, while keeping the surface temperature below ablation level. This new design provided two benefits to our bond test applications. First, it allows the testing of ultra-thin materials with no ablation. Samples under test were validated and documented under a Scanning Electronic Microscope (SEM) under 600× and 950× magnifications respectively. In addition, mathematical models using heat transfer theories, were developed to determine the surface and sub-surface temperatures. Both methods validated our non-ablation achievement. Second, this optics design overcame the problem of power dispersion from a single spot energy source. As illustrated in FIG. 18, energy disperses in all directions from a single point source. With a single detection point positioned at some distance from the source, a theoretical 1/360 power is received for every degree of dispersion. For a detectable signature, high energy must be applied onto the surface, if a single point source is used. As shown in FIG. 19, the line laser source recombines the dispersed energy at the detection point. This approach provides a highly detectable signature at low power density.

The optics design utilizes a succession of cylinder lenses to create an intermediate line image ahead of the objective lens. In the preferred embodiment, the line shaped beams are 1 to 2 mm long. The beam size can be changed by varying the spacing between the negative cylinder and the first positive cylinder. The optics design is based on Code V ray tracing software. This optical system uses a succession of cylinder lenses to create an immediate line image. By varying the focal length of the first lens in the system (the negative cylinder), the F/no. of the immediate image can be varied which in turn controls the width of the beam in the focus of the objective lens. The optics design is shown in Appendix A.

The adherence of coatings on material surfaces is an important problem in many manufacturing settings from automobile to microelectronics circuit manufacturing. Usually these coatings are thin (1–40 microns), and deposited on base materials which have very different optical, chemical, thermal or mechanical properties.

The laser ultrasonic approach of the present invention measures the characteristics of elastic wave propagation within a region that encompasses both the coating and the base material. This is a totally mechanical measurement dependent on mechanical properties, such as coating thickness, elastic constants and the condition of the bond between the coating and its base material. Elastic waves consist of elastic strains that can propagate considerable distances along the coating surface. These strains stretch the coating/substrate interface thereby testing the bond strength directly. Strains both parallel and perpendicular to the interface plane can be applied either together or individually through the use of polarized elastic wave modes on the coating and its base material.

Along the surface of a material, the travelling elastic wave mode is known as a Rayleigh wave. It is much like the waves that propagate on the surface of liquids, such as waves in the ocean, except that the restoring force is elastic rather than surface tension. This wave travels for long distances and does not change its shape, only its amplitude due to attenuation. The speed of this wave depends on the elastic constants of the material.

Figure 20:
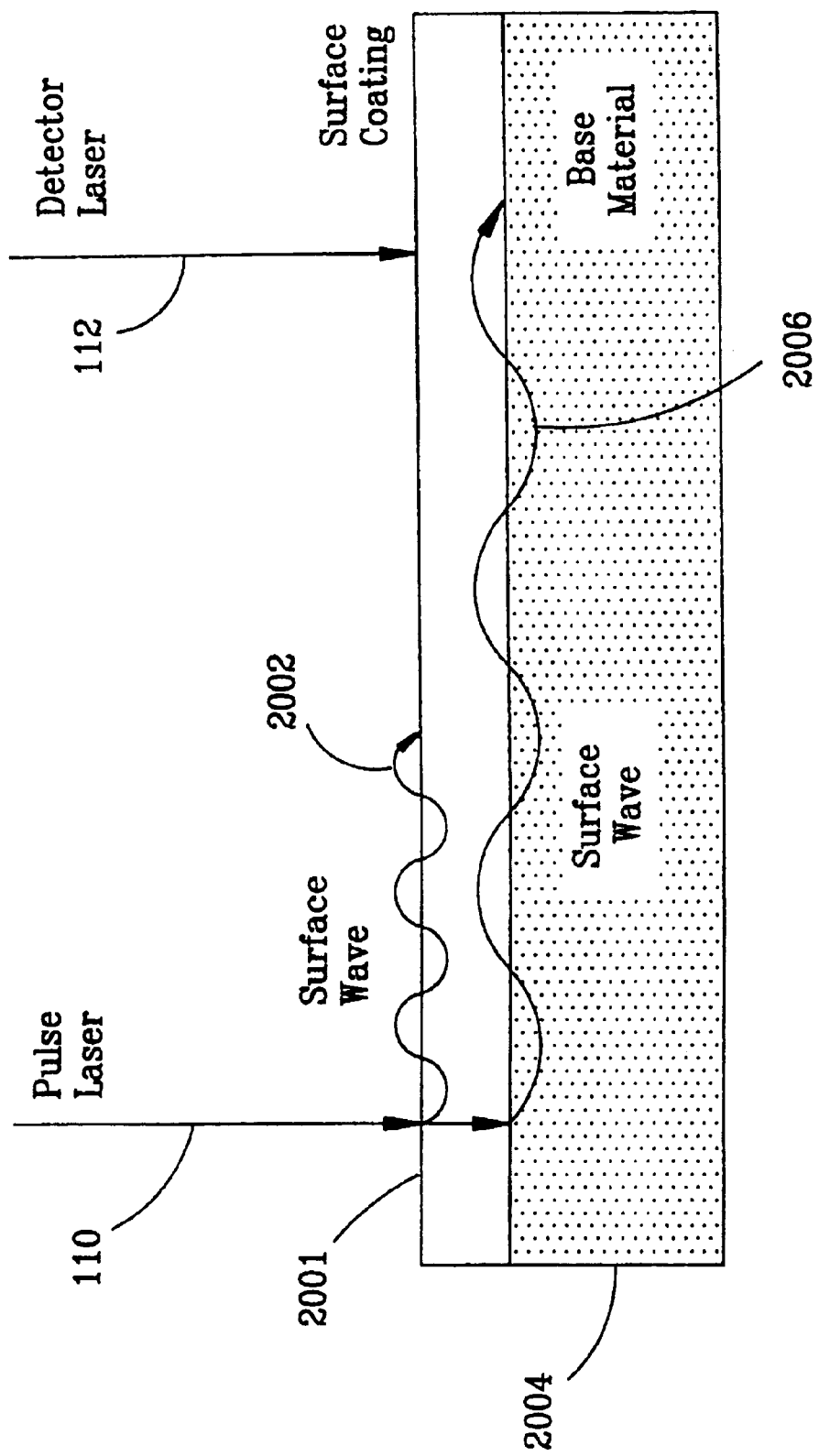
FIG. 20 is a side sectional view showing the application of the laser ultrasonic techniques of the present invention to analysis of a thin coating.

If the coating material is a thin sheet, two surface waves will travel along the material, one on the top surface and the other on the bottom surface. These waves will propagate as surface waves, as illustrated in FIG. 20. This phenomenon can be explained as follows.

As the pulse laser impacts the surface 2001, waves with varying frequencies are generated along the surface 2001 of the coating material. The propagations with wave lengths shorter than the thickness of the coating material stay on top of the coating as shown at 2002 and propagate outwards at the Rayleigh velocity of the coating material. On the other hand, the wavelengths longer than the thickness of the coating material will penetrate through the coating materials onto the base material 2004. Since the base material is normally thicker than the penetrating wave length, these wave frequencies 2006 will travel along the top of the base material at the base material Rayleigh velocity, to the detection point. When this situation occurs, two surface waves 2002 and 2006 can be detected—one arrives at a different speed than the other. Using Fast Fourier Transform (FFT) analysis of these signatures, and correlating to its wavelengths, the thickness of the coating material can be readily determined.

Figure 21:
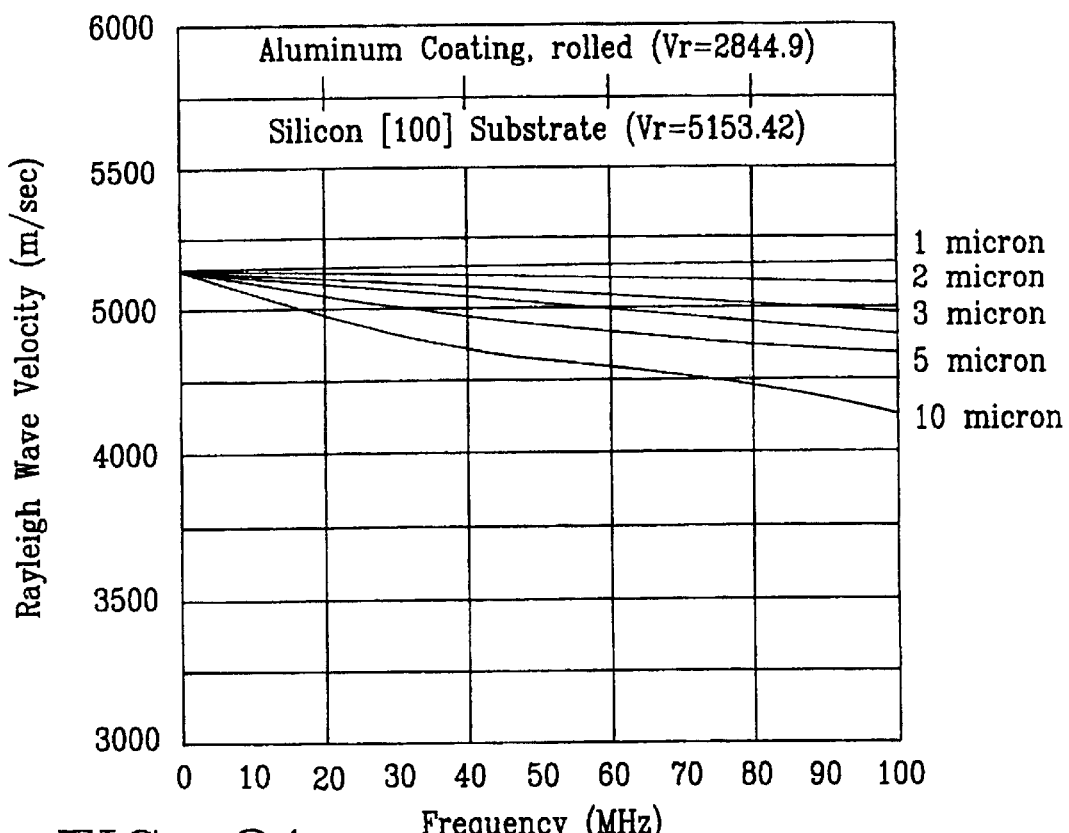
FIG. 21 is an exemplary graph of Rayleigh wave velocity versus frequency for various thicknesses of a thin coating of aluminum on a silicon substrate.

As discussed above, the wave dispersion behaviors make identification of these modes very easy. In addition, the degree of dispersion of these waves are dependent on the thickness of the materials. FIG. 21 shows the Rayleigh wave velocity of a surface wave plotted against the frequency of the wave, when travelling along an aluminum coated silicon material. As indicated, the velocity of the propagation wave slows down as its frequency increases. If one monitors the arrival time of a high frequency component of the wave, say 100 MHz, one can determine the thickness of the coating material. Alternately, the shape of the signature dispersion detected can also be used to determine the thickness of the coating. Sample wave forms in Appendix B illustrate dispersed wave forms on various thickness of aluminum coated silicon. The samples show the wave form at separation distance of 20.0 mils for coating thickness of $1.0\,\mu m$, $5.0\,\mu m$, $10.0\,\mu m$ and $20.0\,\mu m$ respectively. A very different wave form can be detected due to different coating thickness.

Adhesion characteristics of the joining materials can be determined by the disturbance or out of normal asymmetric waveform. For example, if there is total non-adhesion between the coating and base materials, a flat waveform will be detected.

Figure 22:
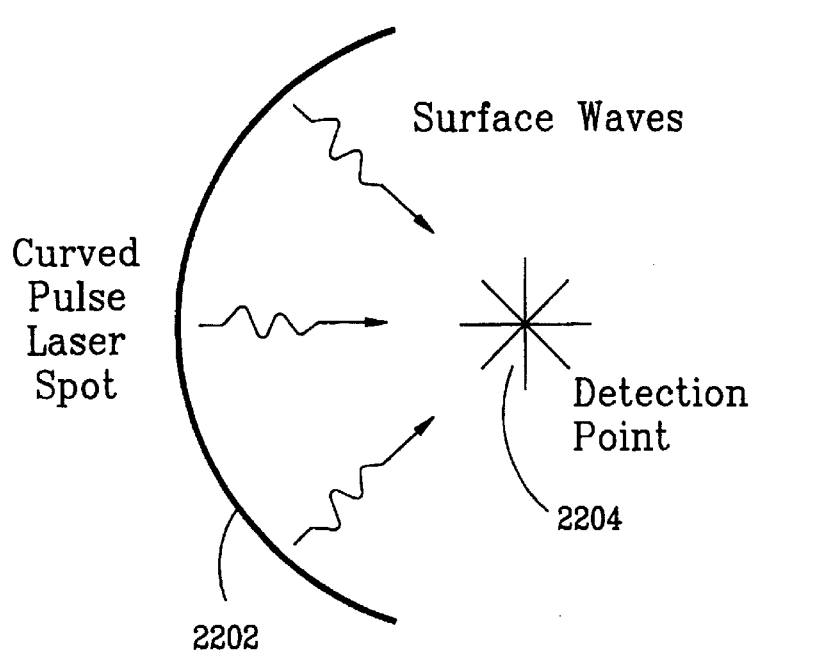
FIG. 22 is a top view of an alternative embodiment of the invention which uses a curved pulse laser spot to create surface waves focused on a single detection point.

In another preferred embodiment of the thin coat testing method, a new laser beam design was made to further improve the signal-to-noise ratio. Instead of a spot or a straight line footprint. A curved line pulse laser foot print was developed. Referring now to FIG. 22, the curved laser 2202 allows the same or better power density on the surface of the materials, the surface wave propagation will be focused to a single detection point 2204. When positioning the detection beam at the focal point of the curved laser beam 2202, the amplitudes of the signatures are summed, thus increasing the signature amplitude many times. This technique is especially useful when the material layers are sensitive to heat induced by the pulse laser. One important criteria for using this technique is that the detector laser foot print must be accurately positioned at the focal point of the curved laser beam. The disadvantage in using this technique is that the curvature of the laser beam has to be changed accordingly when the distance between the pulse and detector laser is changed.

The various embodiments of the invention may incorporate any or all of the features disclosed in the inventor's prior U.S. Pat. No. 5,535,006, U.S. provisional App. No. 60/068, 362 filed Dec. 19, 1997, and/or U.S. non-provisional app. Ser. No. 09/215,374 filed Dec. 18, 1998, the disclosures of which are all incorporated herein by reference.

Thus, there has been disclosed an improved system and method for monitoring interconnections between elements.

The invention is not limited to the specific examples disclosed herein, but includes all variations encompassed by the language of the claims which follow.

What is claimed is:

1. A laser ultrasonic system for evaluating a bond between an element and a substrate, comprising:
    Pulse application means including a collimated light source for transmitting a pulse of light along an optical path to a target point on a substrate;
    Firing detection means in said optical path for detecting the passage of said pulse of light along said optical path and providing an output signal indicating the presence of the pulse;
    Monitoring means for detecting the propagation of vibrations in said substrate, and collecting for analysis a vibration signature reflecting said propagation of said vibrations;
    Synchronization control means connected to said pulse application means and said firing detection means for selectively actuating said pulse application means to provide a light pulse to said target point, monitoring said firing detection means to determine the timing of said pulse transmission, and in response thereto, activating said monitoring means to collect a pertinent part of said vibration signature relative to said timing of said pulse transmission.

2. The laser ultrasonic system in accordance with claim 1, wherein said element comprises a coating bonded to said substrate.

3. The laser ultrasonic system in accordance with claim 1, wherein said element comprises an element from the group consisting of ball bonds, wedge bonds, circuit traces, ribbon bonds, welds, solder balls, surface mount components, pin grid arrays, MIMMS, and adhesion media.

4. The laser ultrasonic system in accordance with claim 2, further comprising:
    means for analyzing said vibration signature to determine the degree of integrity of said bond between said coating and said substrate.

5. The laser ultrasonic system in accordance with claim 4, wherein said means for analyzing comprises means for detecting the presence or absence of a void between said coating and said substrate.

6. The laser ultrasonic system in accordance with claim 4, wherein said means for analyzing comprises means for detecting the presence or absence of a crack in at least one of said coating and said substrate.

7. The laser ultrasonic system in accordance with claim 4, wherein said means for analyzing comprises means for detecting a non-bond and non-contact condition between said coating and said substrate.

8. The laser ultrasonic system in accordance with claim 4, wherein said means for analyzing comprises means for detecting a non-bond-but-in-contact condition between said coating and said substrate.

9. The laser ultrasonic system in accordance with claim 4, wherein said means for analyzing comprises means for detecting a partial bond or full bond condition between said coating and said substrate.

10. The laser ultrasonic system in accordance with claim 2, wherein said coating comprises a thin film coating.

11. The laser ultrasonic system in accordance with claim 10, wherein said thin film coating comprises a metallized thin film coating and wherein said substrate comprises a semiconductor-based substrate.

12. The laser ultrasonic system in accordance with claim 11, wherein said metallized thin film coating comprises an aluminum thin film coating.

13. The laser ultrasonic system in accordance with claim 11, wherein said metallized thin film coating comprises a gold thin film coating.

14. The laser ultrasonic system in accordance with claim 11, wherein said semiconductor-based substrate comprises a silicon-based substrate.

15. The laser ultrasonic system in accordance with claim 11, wherein said semiconductor-based substrate comprises a gallium arsenide-based substrate.

16. The laser ultrasonic system in accordance with claim 2, wherein said target point is a point on said coating.

17. The laser ultrasonic system in accordance with claim 2, further comprising an optical subsystem deployed between said collimated light source and said target point.

18. The laser ultrasonic system in accordance with claim 17, wherein said optical subsystem comprises means for shaping said pulse of light to form an elongated pulse laser spot at said target point, whereby a reduced power density is delivered to said target point.

19. The laser ultrasonic system in accordance with claim 1, further comprising an optical subsystem deployed between said collimated light source and said target point, said optical subsystem controlling the spot size of a detector laser beam associated with said monitoring means.

20. A method for evaluating the integrity of a bond between a substrate and a coating, comprising the steps of:
    Using a collimated light source to apply a pulse of light to a target point on a coated substrate;
    Detecting transmission of said pulse along an optical path between said collimated light source and said target point, and providing an output signal indicating the presence of said pulse;
    Detecting propagation of vibrations in said substrate, and collecting for analysis a vibration signature reflecting said propagation of said vibrations; and,
    Determining timing of said pulse transmission, and in response thereto, activating monitoring means to enable analysis of a pertinent part of said vibration signature relative to said timing of said pulse transmission.

21. The method in accordance with claim 20, further comprising the steps of:
    analyzing said vibration signature to determine the integrity of said bond between said substrate and said coating.

22. The method in accordance with claim 21, wherein said analyzing step comprises a step of applying a frequency-domain analysis to said signature to determine the thickness of said coating.

23. The method in accordance with claim 21, wherein said analyzing step comprises a step of applying a time-domain analysis to said signature to determine the thickness of said coating.

24. A method for evaluating the integrity of a bond between a coating and a substrate, comprising the steps of:
    Using a continuous wave laser and interferometer to produce an interference pattern from light reflected by said coating or said substrate;
    Using a detecting means to monitor changes in said interference pattern over time;
    Selecting a preset point of optimum system sensitivity along the duration of said changes;
    Triggering a collimated light source to apply a pulse to a target point on said coating or said substrate when said selected preset point is reached; and,
    Using said detecting means to detect the propagation of vibrations in said substrate resulting from said pulse, and collecting for analysis a vibration signature reflecting said propagation of said vibrations.

25. The method in accordance with claim 24, wherein said step of applying a pulse to a target point comprises the step of applying a pulse having a curved line foot print.

26. A laser ultrasonic system for evaluating a bond between an element and a substrate, comprising:

Pulse application means including a collimated light source for applying a pulse of light along an optical path to a target point;

Firing detection means in said optical path for detecting the passage of said pulse of light along said optical path and providing an output signal indicating the presence of the pulse;

Monitoring means for detecting the propagation of vibrations in said substrate, and collecting for analysis a vibration signature reflecting said propagation of said vibrations;

Synchronization control means connected to said pulse application means and said firing detection means for selectively actuating said pulse application means to provide a light pulse to said target point, monitoring said firing detection means to determine the timing of said pulse transmission, and in response thereto, activating said monitoring means to collect a pertinent part of said vibration signature relative to said timing of said pulse transmission.

27. The laser ultrasonic system in accordance with claim 26, wherein said element comprises a coating bonded to said substrate.

28. A laser ultrasonic system for evaluating a bond between an element and a substrate, comprising:

Pulse application means including a collimated light source for applying a pulse of light along an optical path to a target point;

Monitoring means for detecting the propagation of vibrations in said substrate, said monitoring means comprising a detection apparatus for collecting a plurality of vibration signatures reflecting said propagation of said vibrations from a plurality of locations around said element;

means for using said plurality of vibration signatures to create a three-dimensional propagation view of said bond between said element and said substrate.

29. The laser ultrasonic system in accordance with claim 28, wherein said detection apparatus comprises a plurality of detectors positioned at said plurality of locations.

30. The laser ultrasonic system in accordance with claim 28, wherein said detection apparatus comprises a single sensor used sequentially to obtain waveform data for each of said plurality of locations.

31. The laser ultrasonic system in accordance with claim 28, wherein said three-dimensional propagation view is correlated or interpreted to the structure of said bond and displayed for viewing.

32. A method for evaluating the integrity of a bond between an element and a substrate, comprising the steps of:

Using a continuous wave laser and interferometer to produce an interference pattern from light reflected by said element, said bond or said substrate;

Triggering a collimated light source to apply a pulse to a target point on said element, said bond or said substrate;

Using a detector to detect said interference pattern and collect for analysis a vibration signature reflecting said propagation of said vibrations; and, extracting information from said vibration signature to determine the integrity of said bond between said element and said substrate.

* * * * *